United States Patent
Meier et al.

(10) Patent No.: US 8,623,343 B2
(45) Date of Patent: Jan. 7, 2014

(54) HIGHLY CATIONIC COPOLYMERS BASED ON QUATERNIZED NITROGEN-CONTAINING MONOMERS

(75) Inventors: Nicole Meier, Mannheim (DE); Ivette Garcia Castro, Ludwigshafen (DE); Claudia Wood, Weinheim (DE); Jessica Staub, Hassloch (DE)

(73) Assignee: BASF SE, Ludwigshafen (DE)

( * ) Notice: Subject to any disclaimer, the term of this patent is extended or adjusted under 35 U.S.C. 154(b) by 365 days.

(21) Appl. No.: 12/669,315

(22) PCT Filed: Jul. 1, 2008

(86) PCT No.: PCT/EP2008/058439
§ 371 (c)(1),
(2), (4) Date: Jan. 15, 2010

(87) PCT Pub. No.: WO2009/010385
PCT Pub. Date: Jan. 22, 2009

(65) Prior Publication Data
US 2010/0209361 A1    Aug. 19, 2010

(30) Foreign Application Priority Data
Jul. 17, 2007 (EP) .................................... 07112639

(51) Int. Cl.
*C11D 1/62* (2006.01)
*A61K 47/32* (2006.01)
*A61K 8/81* (2006.01)

(52) U.S. Cl.
CPC .................................... *A61K 8/8141* (2013.01)
USPC ..................................... 424/70.28; 514/772.4

(58) Field of Classification Search
None
See application file for complete search history.

(56) References Cited

U.S. PATENT DOCUMENTS 4,058,491 A * 11/1977 Steckler ......................... 521/38
5,846,924 A * 12/1998 Detering et al. ............. 510/475
2008/0199416 A1* 8/2008 Nguyen Kim et al. .... 424/70.11

FOREIGN PATENT DOCUMENTS

| DE | 102 41 296 A1 | 3/2004 | |
| WO | WO-93/25595 A1 | 12/1993 | |
| WO | WO-95/27759 A1 | 10/1995 | |
| WO | WO-00/42985 A1 | 7/2000 | |
| WO | WO-2005/005497 A1 | 1/2005 | |
| WO | WO-2006/097514 A1 | 9/2006 | |
| WO | WO 2007/010035 | * 1/2007 | ............... A61K 8/81 |

* cited by examiner

*Primary Examiner* — Brian Gulledge
(74) *Attorney, Agent, or Firm* — Novak Druce Connolly Bove + Quigg LLP

(57) ABSTRACT

The present invention relates to a copolymer with high cationic charge based on quaternized nitrogen-containing monomers, to cosmetic or pharmaceutical compositions which comprise at least one such copolymer, and to further uses of these copolymers.

23 Claims, No Drawings

HIGHLY CATIONIC COPOLYMERS BASED ON QUATERNIZED NITROGEN-CONTAINING MONOMERS

CROSS REFERENCE TO RELATED APPLICATIONS

This application is a national phase of PCT/EP2008/058439, filed on Jul. 1, 2008 which claims priority to EP 07112639.5 filed Jul. 17, 2007, the entire contents of all are hereby incorporated by reference.

DESCRIPTION

The present invention relates to a copolymer with high cationic charge based on quaternized nitrogen-containing monomers, to cosmetic or pharmaceutical compositions which comprise at least one such copolymer, and to further uses of these copolymers.

Cosmetically and pharmaceutically acceptable water-soluble polymers serve, for example in soaps, creams and lotions, as formulation means, e.g. as thickener, foam stabilizer or water absorbent, or else to alleviate the irritative effect of other ingredients or to improve the dermal application of active ingredients. Their task in hair cosmetics is to influence the properties of the hair. In pharmacy, they serve, for example, as coating compositions or binders for solid drug forms.

For hair cosmetics, film-forming polymers with ionic groups are used, for example, as conditioners in order to improve the dry and wet combability, the feel to the touch, the shine and the appearance of the hair, and also to impart antistatic properties to the hair. Depending on the intended use, water-soluble polymers with cationic or anionic functionalities are used here. Thus, as a consequence of their structure, polymers with cationic functional groups have high affinity to the negatively charged surface of the hair.

The provision of products with a complex profile of properties often presents difficulties. Thus, there is a need for polymers for hair cosmetic compositions which are capable of forming essentially smooth, nonsticky films and which simultaneously impart to the hair good sensorialy perceptible properties, such as elasticity, a pleasant feel, and also antistatic properties. Furthermore, the dry and wet combability, the feel to the touch, the shine and the appearance of the hair are to be improved.

If these polymers are to be used in hairspray formulations, then additionally good propellant gas compatibility, suitability for use in low-VOC formulations, good solubility in water or aqueous/alcoholic solvent mixtures and good ability to be washed out is desired. Likewise, a build-up effect is to be kept as low as possible.

In many cases, the desired profile of properties can only be achieved through the use of a plurality of cosmetically active components, for example a plurality of polymers with ionic groups. However, incompatibility of the various components with one another often arises, which can lead, for example, to clear formulations no longer being able to be prepared. The use of a plurality of polyelectrolytes that are not adequately compatible with one another can lead to undesired salting out. Thus, cationic polymers in particular are also essential constituents of shampoos, which generally also comprise anionic surfactants. In many cases, incompatibilities between the cationic polymers and these anionic surfactants then lead to inadequate storage stability of the preparations.

WO 00/42985 describes, on pp. 19-20, numerous cationic polymers which are suitable as conditioners in cosmetic preparations. Mention is made of commercially available polymers such as Jaguar®C-14-S, Jaguar®C-17, Jaguar®C-16, das Ucare Polymer JR-30M, JR-400, LR400, Catanal, Celquat, Merquat®100, Merquat®550, Merquat®S, Merquat®3330, Merquat®2001, Gafquat®755N, Luviquat®FC370, Polyquatemium 2, polyalkylenimines, Aqualon®N-Hance.

However, the terpolymers of the present invention are not described.

DE 102 41 296 describes water-in-water emulsion polymers of N-vinylpyrrolidone and Quat-311 or of N-vinylpyrrolidone and quaternized N-vinylimidazole which are suitable as conditioners. Furthermore, this specification specifies, in paragraph [0191], numerous further cationic copolymers as conditioners customary in shampoos. However, the terpolymers of the present invention are not described.

WO 2005/005497 describes an aqueous polymer dispersion Pd) which is obtainable by free-radical polymerization of a monomer mixture M), comprising
a) at least one $\alpha,\beta$-ethylenically unsaturated amide-group-containing compound of the general formula I

where
$R^2$ is a group of the formula $CH_2=CR^4$—, and $R^1$ and $R^3$, independently of one another, are H, alkyl, cycloalkyl, heterocycloalkyl, aryl or hetaryl, or
$R^1$ and $R^3$, together with the amide group to which they are bonded, are a lactam having 5 to 8 ring atoms,
b) at least one free-radically polymerizable crosslinking compound with at least two $\alpha,\beta$-ethylenically unsaturated double bonds per molecule,
c) at least one compound with a free-radically polymerizable $\alpha,\beta$-ethylenically unsaturated double bond and at least one cationogenic and/or cationic group per molecule,
in an aqueous medium in the presence of at least one polymeric anionic dispersant D). They are suitable as conditioners for cosmetic preparations, in particular shampoos.

Copolymers which comprise both monomers of type a) and of type b) in copolymerized form are not described.

WO 06/097514 relates to the use of a water-soluble or water-dispersible crosslinked polymer obtainable by polymerization of a mixture comprising 99.99 to 10% by weight of at least one $\alpha,\beta$-ethylenically unsaturated compound with at least one cationogenic and/or cationic group per molecule, 0 to 90% by weight of at least one monoethylenically unsaturated amide-group-containing compound different from a), and 0.01 to 5% by weight of a crosslinker for modifying the rheology of aqueous, alcoholic or aqueous/alcoholic compositions.

Copolymers which comprise both monomers of type a) and of type b) in copolymerized form are not described.

Despite extensive efforts, there continues to be a need for improvement for polymers known from the prior art for conditioners and shampoos. Good properties are desired with regard to the conditioning of the hair in its sensorialy perceptible properties such as feel, volume, manageability etc. Furthermore, the polymers should be characterized by good compatibility with other formulation constituents.

Surprisingly, it has been found that of suitability for the requirements specified above are in particular copolymers which are obtainable by polymerization of
a) at least one α,β-ethylenically unsaturated monomer a) of the general formula I

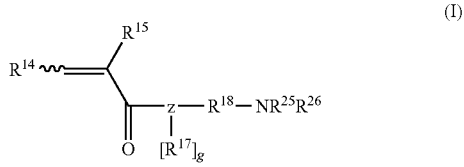

where
$R^{14}$ and $R^{15}$, independently of one another, are selected from the group consisting of hydrogen, C1-C8 linear- or branched-chain alkyl, methoxy, ethoxy, 2-hydroxyethoxy, 2-methoxyethoxy and 2-ethoxyethyl,
$R^{17}$ is hydrogen or methyl,
$R^{18}$ is alkylene or hydroxyalkylene having 1 to 24 carbon atoms, optionally substituted by alkyl, preferably $C_2H_4$, $C_3H_6$, $C_4H_8$, $CH_2$—CH(OH)—$CH_2$,
g is 0 or 1,
Z is nitrogen when g=1 or oxygen when g=0,
$R^{25}$ and $R^{26}$ are in each case and independently of one another selected from the group consisting of hydrogen, C1-C40 linear- or branched-chain alkyl, formyl, C1-C10 linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl,
where at least 60% of the nitrogen atoms of a) are quaternary nitrogen atoms,
b) at least one α,β-ethylenically unsaturated monomer b) of the general formula II

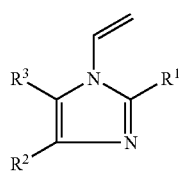

where $R^1$ to $R^3$, independently of one another, are hydrogen, $C_1$-$C_4$-alkyl or phenyl;
c) at least one α,β-ethylenically unsaturated monomer c) of the general formula III

where
one of the radicals $R^4$ to $R^6$ is a group of the formula $CH_2$=$CR^7$— where $R^7$=H or $C_1$-$C_4$-alkyl and the other radicals $R^4$ to $R^6$, independently of one another, are H, alkyl, cycloalkyl, heterocycloalkyl, aryl or hetaryl,
where $R^4$ and $R^5$, together with the amide group to which they are bonded may also be a lactam having 5 to 8 ring atoms, where $R^5$ and $R^6$, together with the nitrogen atom to which they are bonded, may also be a five- to seven-membered heterocycle,
d) if appropriate at least one further free-radically polymerizable monomer d) different from a), b) and c).

For the purposes of the present invention, the expression alkyl comprises straight-chain and branched alkyl groups. Suitable short-chain alkyl groups are, for example, straight-chain or branched $C_1$-$C_7$-alkyl groups, preferably $C_1$-$C_6$-alkyl groups and particularly preferably $C_1$-$C_4$-alkyl groups. These include, in particular, methyl, ethyl, propyl, isopropyl, n-butyl, isobutyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 2-ethylpentyl, 1-propylbutyl, octyl etc.

Branched $C_3$-$C_5$-alkyl is preferably isopropyl, isobutyl, sec-butyl, tert-butyl, 1-methylbutyl, 2-methylbutyl, 3-methylbutyl, 1,2-dimethylpropyl, 1,1-dimethylpropyl, 2,2-dimethylpropyl, 1-ethylpropyl. Preference is given to tert-butyl.

Suitable longer-chain $C_8$-$C_{30}$-alkyl groups or $C_8$-$C_{30}$-alkenyl groups are straight-chain and branched alkyl or alkenyl groups. These are preferably predominantly linear alkyl radicals as also occur in natural or synthetic fatty acids and fatty alcohols, and also oxo alcohols which may, if appropriate, additionally be mono-, di- or polyunsaturated. These include, for example, n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene), arachinyl(ene), behenyl(ene), lignocerinyl(ene), melissinyl(ene), etc.

Cycloalkyl is preferably $C_5$-$C_8$-cycloalkyl, such as cyclopentyl, cyclohexyl, cycloheptyl or cyclooctyl.

Aryl comprises unsubstituted and substituted aryl groups and is preferably phenyl, tolyl, xylyl, mesityl, naphthyl, fluorenyl, anthracenyl, phenanthrenyl, naphthacenyl and in particular phenyl, tolyl, xylyl or mesityl.

In the text below, compounds which are derived from acrylic acid and methacrylic acid may sometimes be referred to for short by adding the syllable "(meth)" to the compound derived from acrylic acid.

For the purposes of the present invention, water-soluble monomers and polymers are understood as meaning monomers and polymers which dissolve to at least 1 g/l at 20° C. in water. Water-dispersible monomers and polymers are understood as meaning monomers and polymers which disintegrate into dispersible particles under the application of shear forces, for example by stirring. Hydrophilic monomers are preferably water-soluble or at least water-dispersible.

In one specific embodiment, the copolymers according to the invention have no silicon-atom-containing groups.

According to the invention, at least 60%, preferably 75%, further preferably 90% and in particular at least 95%, of the nitrogen atoms of monomer a) are quaternary nitrogen atoms, in particular quaternary ammonium groups. Quaternary ammonium groups are understood by the person skilled in the art as meaning charged cationic groups which can be produced from amine nitrogen atoms by quaternization with alkylating agents. Suitable alkylating agents are $C_1$-$C_4$-alkyl halides or sulfates, such as ethyl chloride, ethyl bromide, methyl chloride, methyl bromide, dimethyl sulfate and diethyl sulfate.

A preferred quaternizing agent is methyl chloride. Another preferred quaternizing agent is diethyl sulfate.

Charged cationic groups (but not quaternary ammonium groups for the purposes of the invention) can be produced from the amine nitrogens also by protonation with acids.

Suitable acids are, for example, carboxylic acids, such as lactic acid, or mineral acids, such as phosphoric acid, sulfuric acid and hydrochloric acid.

According to the invention, at least 60 mol %, preferably 75 mol %, further preferably 90 mol % and in particular at least 95 mol % of monomer a) have the following structural formula:

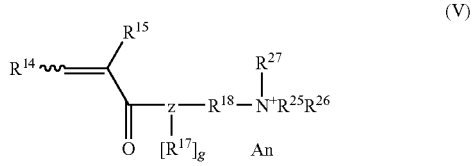

(V)

where $R^{27}$ is H, $C_1$-$C_4$-alkyl, preferably methyl or ethyl
and An is halogen ion, preferably $Cl^-$, $CH_3SO_4^-$, $C_2H_5SO_4^-$, $(SO_4^{2-})_{0.5}$ Monomer a)

Preferred monomers a) are esters of (meth)acrylic acid with amino alcohols mono- or di-$C_1$-$C_{24}$-alkyl-substituted on the nitrogen. These are particularly preferably selected from the group consisting of N-methylaminoethyl (meth)acrylate, N-ethylaminoethyl (meth)acrylate, N-(n-propyl)aminoethyl (meth)acrylate, N-(n-butyl)aminoethyl (meth)acrylate, N-(tert-butyl)aminoethyl (meth)acrylate, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate and N,N-dimethylaminocyclohexyl (meth)acrylate. Particular preference is given to N,N-dimethylaminoethyl methacrylate.

Further preferred monomers a) are amides of (meth)acrylic acid with diamines mono- or di-$C_1$-$C_{24}$-alkyl-substituted on the nitrogen. These are particularly preferably selected from the group consisting of N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]meth-acrylamide, N-[8-(dimethylamino)octyl]methacrylamide, N-[12-(dimethylamino)dodecyl]methacrylamide, N-[3-(diethylamino)propyl]methacrylamide and N-[3-(diethylamino)propyl]acrylamide. Particular preference is given to N-[3-(dimethylamino)propyl]methacrylamide.

According to the invention, at least 60 mol %, preferably 75 mol %, further preferably 90 mol % and in particular at least 95 mol % of monomer a), based on the total amount of all monomers a), have at least one quaternary nitrogen atom.

Preferably, at least one monomer a) is selected from quaternized N,N-dimethylaminoethyl (meth)acrylate, quaternized N-[3-(dimethylamino)propyl](meth)acrylamide and mixtures thereof.

Furthermore, monomer a) preferably is or comprises N,N-dimethylaminoethyl (meth)acrylate quaternized with methyl chloride, dimethyl sulfate or diethyl sulfate.

Specifically, monomer a) is or comprises N,N-dimethylaminoethyl methacrylate quaternized with methyl chloride.

The copolymers according to the invention comprise preferably at least 60% by weight, further preferably at least 65% by weight and in particular at least 70% by weight, based on the total weight of the monomers used for the polymerization, of at least one monomer a) in copolymerized form.

The copolymers according to the invention preferably comprise at most 90% by weight, further preferably at most 85% by weight and in particular at most 80% by weight, based on the total weight of the monomers used for the polymerization, of at least one monomer a) in copolymerized form.

Monomer b)

The copolymers according to the invention comprise, as compound b), at least one α,β-ethylenically unsaturated monomer b) of the general formula II in copolymerized form

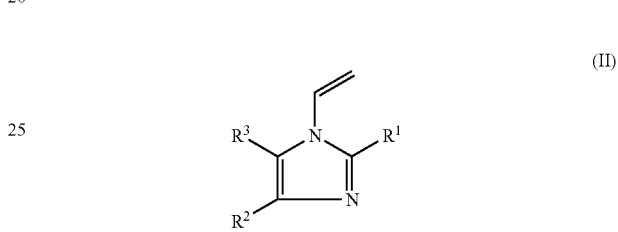

(II)

where $R^1$ to $R^3$, independently of one another, are hydrogen, $C_1$-$C_4$-alkyl or phenyl.

Examples of suitable compounds of the general formula (II) are given in Table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

As monomer b), 1-vinylimidazole (N-vinylimidazole) and mixtures which comprise N-vinylimidazole are preferred.

The copolymers according to the invention comprise preferably at least 5% by weight, further preferably at least 7.5% by weight and in particular at least 10% by weight, based on the total weight of the monomers used for the polymerization, of at least one monomer b) in copolymerized form.

The copolymers according to the invention comprise preferably at most 20% by weight, further preferably at most 17.5% by weight and in particular at most 15% by weight, based on the total weight of the monomers used for the polymerization, of at least one monomer b) in copolymerized form.

In one embodiment of the invention, the monomers b) can also carry cationic charges. Here, the nitrogen atom located at the double bond in the general formula II carries a further substituent, preferably methyl or ethyl. Such monomers b) are, for example, 3-methyl-1-vinylimidazolium chloride, methosulfate and ethosulfate.

In a preferred embodiment of the invention, at most 20 mol %, further preferably at most 10 mol %, particularly preferably at most 5 mol % and in particular at most 1 mol %, of the monomers b) have a quaternary nitrogen atom. It is most preferred to use monomer b) in nonquaternized state for the polymerization.

Monomer c)

Preferred monomers c) are open-chain N-vinylamide compounds, such as N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide, N-vinylbutyramide and mixtures thereof.

Further preferred monomers c) are selected from the group consisting of acrylamide, the N-vinyl derivatives of optionally alkyl-substituted 2-pyrrolidone, optionally alkyl-substituted 2-piperidone and optionally alkyl-substituted ε-caprolactam.

Furthermore preferred monomers c) are selected from the group consisting of the N-vinyl derivatives of 2-pyrrolidone, 3-methyl-2-pyrrolidone, 4-methyl-2-pyrrolidone, 5-methyl-2-pyrrolidone, 3-ethyl-2-pyrrolidone, 3-propyl-2-pyrrolidone, 3-butyl-2-pyrrolidone, 3,3-dimethyl-2-pyrrolidone, 3,5-dimethyl-2-pyrrolidone, 5,5-dimethyl-2-pyrrolidone, 3,3,5-trimethyl-2-pyrrolidone, 5-methyl-5-ethyl-2-pyrrolidone, 3,4,5-trimethyl-2-pyrrolidone, 3-methyl-2-piperidone, 4-methyl-2-piperidone, 5-methyl-2-piperidone, 6-methyl-2-piperidone, 6-ethyl-2-piperidone, 3,5-dimethyl-2-piperidone, 4,4-dimethyl-2-piperidone, 3-methyl-ε-caprolactam, 4-methyl-ε-caprolactam, 5-methyl-ε-caprolactam, 6-methyl-ε-caprolactam, 7-methyl-ε-caprolactam, 3-ethyl-ε-caprolactam, 3-propyl-ε-caprolactam, 3-butyl-ε-caprolactam, 3,3-dimethyl-ε-caprolactam, 7,7-dimethyl-ε-caprolactam and mixtures thereof.

Particularly preferably, monomer c) is or comprises N-vinylpyrrolidone or N-vinylcaprolactam. Most preferably, monomer c) is or comprises N-vinylpyrrolidone.

Monomer d)

The copolymers according to the invention comprise, if appropriate, at least one further free-radically polymerizable monomer d) different from a), b) and c) in copolymerized form.

The copolymers according to the invention can additionally comprise, in copolymerized form, at least one monomer e) different from components a) to d) and copolymerizable therewith.

Monomer d) is, for example, selected from esters, different from a) to c), of α,β-ethylenically unsaturated mono- and dicarboxylic acids with $C_1$-$C_{30}$-alkanols and $C_1$-$C_{30}$-alkanediols, amides of α,β-ethylenically unsaturated mono- and dicarboxylic acids with $C_2$-$C_{30}$-aminoalcohols which have a primary or secondary amino group, esters of vinyl alcohol and allyl alcohol with $C_1$-$C_{30}$-monocarboxylic acids, vinyl ethers, vinyl aromatics, vinyl halides, vinylidene halides, $C_1$-$C_8$-monoolefins, nonaromatic hydrocarbons with at least two conjugated double bonds and mixtures thereof. Suitable monomers d) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable additional monomers d) are furthermore 2-hydroxyethylacrylamide, 2-hydroxyethylmethacrylamide, 2-hydroxyethylethacrylamide, 2-hydroxypropyl-acrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexyl-acrylamide, 6-hydroxyhexylmethacrylamide, 3-hydroxy-2-ethylhexylacrylamide and 3-hydroxy-2-ethylhexylmethacrylamide.

Suitable monomers d) are also polyether acrylates, which, for the purposes of this invention, are generally understood as meaning esters of α,β-ethylenically unsaturated mono- and dicarboxylic acids with polyetherols. Suitable polyetherols are linear or branched substances having terminal hydroxyl groups which comprise ether bonds. In general, they have a molecular weight in the range from about 150 to 20 000. Suitable polyetherols are polyalkylene glycols, such as polyethylene glycols, polypropylene glycols, polytetrahydrofurans and alkylene oxide copolymers. Suitable alkylene oxides for producing alkylene oxide copolymers are, for example, ethylene oxide, propylene oxide, epichlorohydrin, 1,2- and 2,3-butylene oxide. The alkylene oxide copolymers can comprise the copolymerized alkylene oxide units in statistical distribution or in the form of blocks. Preference is given to ethylene oxide/propylene oxide copolymers.

Suitable monomers d) are also polyether acrylates of the general formula IV

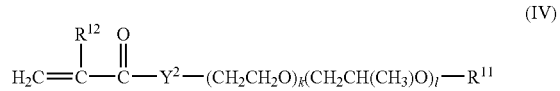

(IV)

in which
the order of the alkylene oxide units is arbitrary,
k and l, independently of one another, are an integer from 0 to 1000, where the sum of k and l is at least 5,
$R^{11}$ is hydrogen, $C_1$-$C_{30}$-alkyl or $C_5$-$C_8$-cycloalkyl,
$R^{12}$ is hydrogen or $C_1$-$C_8$-alkyl,
$Y^2$ is O or $NR^{13}$, where $R^{13}$ is hydrogen, $C_1$-$C_{30}$-alkyl or $C_5$-$C_8$-cycloalkyl.

Preferably, k is an integer from 1 to 500, in particular 3 to 250. Preferably, l is an integer from 0 to 100. Preferably, $R^{12}$ is hydrogen, methyl, ethyl, n-propyl, isopropyl, n-butyl, sec-butyl, tert-butyl, n-pentyl or n-hexyl, in particular hydrogen, methyl or ethyl. Preferably, $R^{11}$ in the formula II is hydrogen, methyl, ethyl, n-propyl, isopropyl, n-butyl, sec-butyl, n-pentyl, n-hexyl, octyl, 2-ethylhexyl, decyl, lauryl, palmityl or stearyl. Preferably, $Y^2$ in the formula II is O or NH.

Suitable polyether acrylates d) are, for example, the polycondensation products of the abovementioned α,β-ethylenically unsaturated mono- and/or dicarboxylic acids and their acid chlorides, acid amides and anhydrides with polyetherols. Suitable polyetherols can be readily produced by reacting ethylene oxide, 1,2-propylene oxide and/or epichlorohydrin with a starter molecule, such as water or a short-chain alcohol $R^{11}$—OH. The alkylene oxides can be used individually, alternately one after the other or as a mixture. The polyether acrylates d) can be used on their own or in mixtures for producing the polymers used according to the invention.

Suitable additional monomers d) are methyl (meth)acrylate, methyl ethacrylate, ethyl (meth)acrylate, ethyl ethacrylate, n-butyl (meth)acrylate, tert-butyl methacrylate, tert-butyl ethacrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate and mixtures thereof. Preferred monomers e) are the esters of $\alpha,\beta$-ethylenically unsaturated mono- and dicarboxylic acids with $C_1$-$C_4$-alkanols.

Suitable additional monomers d) are furthermore vinyl acetate, vinyl propionate, vinyl butyrate and mixtures thereof.

Suitable additional monomers d) are furthermore ethylene, propylene, isobutylene, butadiene, styrene, $\alpha$-methylstyrene, acrylonitrile, methacrylonitrile, vinyl chloride, vinylidene chloride, vinyl fluoride, vinylidene fluoride and mixtures thereof.

Preferred monomers d) are compounds with a free-radically polymerizable, $\alpha,\beta$-ethylenically unsaturated double bond and at least one anionogenic and/or anionic group per molecule.

Preferably, component d) comprises at least one compound which is selected from monoethylenically unsaturated carboxylic acids, sulfonic acids, phosphonic acids and mixtures thereof. Monomers d) include monoethylenically unsaturated mono- and dicarboxylic acids with 3 to 25, preferably 3 to 6, carbon atoms, which can also be used in the form of their salts or anhydrides. Examples thereof are acrylic acid, methacrylic acid, ethacrylic acid, $\alpha$-chloroacrylic acid, crotonic acid, maleic acid, maleic anhydride, itaconic acid, citraconic acid, mesaconic acid, glutaconic acid, aconitic acid and fumaric acid. The monomers d) furthermore include the half-esters of monoethylenically unsaturated dicarboxylic acids with 4 to 10, preferably 4 to 6, carbon atoms, e.g. of maleic acid, such as monomethyl maleate. The monomers d) also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid and allylphosphonic acid. The monomers d) also include the salts of the abovementioned acids, in particular the sodium, potassium and ammonium salts, and also the salts with amines. The monomers d) can be used as such or as mixtures with one another. The stated weight fractions all refer to the acid form.

Preferably, d) is or comprises at least one compound which is selected from acrylic acid, methacrylic acid, ethacrylic acid, $\alpha$-chloroacrylic acid, crotonic acid, maleic acid, maleic anhydride, fumaric acid, itaconic acid, citraconic acid, mesaconic acid, glutaconic acid, aconitic acid, 2-acrylamido-2-methylpropanesulfonic acid, vinylphosphonic acid and mixtures thereof.

Particularly preferably, d) is or comprises at least one compound which is selected from acrylic acid, methacrylic acid and mixtures thereof. In a specific embodiment, d) is or comprises methacrylic acid.

The abovementioned additional monomers d) can be used individually or in the form of any mixtures.

The amount of monomers d) used for the polymerization is at most 20% by weight, preferably at most 15% by weight and particularly preferably at most 10% by weight, in each case based on the total amount of all of the monomers used for the polymerization.

The amount of monomers d) used for the polymerization is at least 0% by weight, preferably at least 3% by weight and particularly preferably at least 5% by weight, in each case based on the total amount of all of the monomers used for the polymerization.

Crosslinker e)

The copolymers according to the invention can, if desired, comprise, in copolymerized form, at least one crosslinker, i.e. a compound with two or more than two ethylenically unsaturated, nonconjugated double bonds.

Preferably, crosslinkers are used in an amount of from 0.01 to 2% by weight, particularly preferably 0.1 to 1% by weight, based on the total weight of the monomers used for the polymerization.

Suitable crosslinkers e) are, for example, acrylic esters, methacrylic esters, allyl ethers or vinyl ethers of at least dihydric alcohols. The OH groups of the parent alcohols may here be completely or partially etherified or esterified; however, the crosslinkers comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and also polyethylene glycols, polypropylene glycols and polytetrahydrofurans with molecular weights of in each case from 200 to 10 000. Apart from the homopolymers of ethylene oxide or propylene oxide, it is also possible to use block copolymers of ethylene oxide or propylene oxide or copolymers which comprise ethylene oxide and propylene oxide groups in incorporated form. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, gluclose, mannose. The polyhydric alcohols can of course also be used following reaction with ethylene oxide or propylene oxide as the corresponding ethoxylates or propoxylates. The polyhydric alcohols can also firstly be converted to the corresponding glycidyl ethers by reaction with epichlorohydrin.

Further suitable crosslinkers e) are the vinyl esters or the esters of monohydric, unsaturated alcohols with ethylenically unsaturated $C_3$-$C_8$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers e) are esters of unsaturated carboxylic acids with the above described polyhydric alcohols, for example oleic acid, crotonic acid, cinnamic acid or 10-undecenoic acid.

Further suitable crosslinkers e) are urethane diacrylates and urethane polyacrylates, as are commercially available, for example, under the name Laromer®.

Furthermore suitable as crosslinker e) are straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Also suitable as crosslinker e) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable as crosslinker e) are triallylamine and triallylmonoalkylammonium salts, e.g. triallylmethylammonium chloride or methylsulfate.

Also suitable are N-vinyl compounds of urea derivatives, at least difunctional amides, cyanurates or urethanes, for example of urea, ethyleneurea, propyleneurea or tartar diamide, e.g. N,N'-divinylethyleneurea or N,N'-divinylpropyleneurea.

Further suitable crosslinkers e) are divinyldioxane, tetraallylsilane or tetravinylsilane.

It is of course also possible to use mixtures of the abovementioned compounds e).

Particularly preferably used crosslinkers e) are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic acid esters and acrylic acid esters of polyalkylene oxides or polyhydric alcohols which have been reacted with ethylene oxide and/or propylene oxide and/or epichlorohydrin.

Very particularly preferred crosslinkers e) are pentaerythritol triallyl ether, methylene-bisacrylamide, N,N'-divinylethyleneurea, triallylamine and triallylmonoalkylammonium salts and acrylic acid esters of glycol, butanediol, trimethylolpropane or glycerol or acrylic acid esters of glycol, butanediol, trimethylolpropane or glycerol reacted with ethylene oxide and/or epichlorohydrin.

Solution Polymerization

Preferably, the polymers are prepared by solution polymerization in aqueous solution.

In a preferred embodiment of the invention, the solvent comprises water and alcohol.

Suitable alcohols are, for example, methanol, ethanol, n-propanol, isopropanol, n-butanol, sec-butanol, tert-butanol, 3-methyl-1-butanol (isoamyl alcohol), n-hexanol, cyclohexanol or glycols, such as ethylene glycol, propylene glycol and butylene glycol, and alkyl ethers of polyhydric alcohols, such as diethylene glycol, triethylene glycol, polyethylene glycols with number-average molecular weights up to about 3000, glycerol.

Particularly preferably, the alcohol is or comprises ethanol and/or isopropanol, in particular isopropanol. The alcohol fraction of the total amount of solvent is in the range from 0 to 50% by weight, preferably from 5 to 40% by weight, particularly preferably from 10 to 30% by weight, in each case based on the total amount of solvent.

In addition to alcohol and water, further solvents may be present in the polymerization solution. Of suitability in principle are all solvents suitable for the free-radical polymerization, such as, for example, acetone, acetonitrile, aniline, anisol, benzonitrile, tert-butyl methyl ether (TBME), gamma-butyrolactone, quinoline, chloroform, cyclohexane, diethyl ether, dimethylacetamide, dimethylformamide, dimethyl sulfoxide, dioxane, ethyl acetate, ethylene dichloride, ethylene glycol dimethyl ether, formamide, hexane, methylene chloride, methyl ethyl ketone, N-methylformamide, petroleum ether/light benzine, propylene carbonate (4-methyl-1,3-dioxol-2-one), sulfolane, tetrachloroethene, tetrachloromethane, tetrahydrofuran, toluene, 1,1,1-trichloroethane, trichloroethene, triethylene glycol dimethyl ether (triglyme) and mixtures thereof.

Polymerization solution is understood as meaning the substance mixture which is present following the addition of all of the components and following completion of the polymerization and before the first work-up step, such as, for example, a drying, a neutralization or a steam distillation.

The amount of water is preferably in the range from 100 to 50% by weight, particularly preferably in the range from 90 to 60% by weight, based on the solvent. The amount of alcohol is preferably in the range from 0 to 50% by weight, particularly preferably in the range from 10 to 40% by weight, based on the solvent.

The amount of substances furthermore present in the polymerization solution, which are essentially the monomers a) to d), the initiator and, if appropriate, regulator and crosslinker, is preferably at least 5% by weight, particularly preferably at least 10% by weight and in particular at least 20% by weight and preferably at most 55% by weight, particularly preferably at most 50% by weight and in particular at most 45% by weight, of the polymerization solution.

This amount can also be referred to as solids content of the polymerization solution.

Preference is given to a method according to the invention in which the temperature of the polymerization solution is in the range from 30° C. to 120° C., particularly preferably in the range from 50° C. to 110° C. and in particular in the range from 70° C. to 100° C.

The polymerization usually takes place under atmospheric pressure, although it can also proceed under reduced or increased pressure. A suitable pressure range is between 1 and 10 bar.

The initiator used for the free-radical polymerization is preferably at least one water-soluble polymerization initiator selected from the group consisting of peroxides, hydroperoxides, peroxodisulfates, percarbonates, peroxide esters, azo compounds and mixtures thereof.

A water-soluble polymerization initiator is understood as meaning an initiator which is soluble at 20° C. and 1013 mbar to at least 1 g, preferably to at least 10 g, in 1 liter of water.

In a preferred embodiment of the invention, the water-soluble polymerization initiator is selected from the group consisting of water-soluble azo compounds, hydrogen peroxide, lithium peroxodisulfate, sodium peroxodisulfate, potassium peroxodisulfate, ammonium peroxodisulfate and mixtures thereof.

The water-soluble polymerization initiator is further preferably selected from the group consisting of 2,2'-azobis[2-(5-methyl-2-imidazolin-2-yl)propane] dihydrochloride 2,2'-azobis[2-(2-imidazolin-2-yl)propane] dihydrochloride 2,2'- azobis[2-(2-imidazolin-2-yl)propane disulfate dihydrate 2,2'-azobis(2-methylpropionamide) dihydrochloride 2,2'-azobis[N-(2-carboxyethyl)-2-methylpropionamidine]tetrahydrate 2,2'-azobis[2-(3,4,5,6-tetrahydropyrimidin-2-yl)propane] dihydrochloride 2,2'-azobis[2-(1-(2-hydroxyethyl)-2-imidazolin-2-yl]propane) dihydrochloride 2,2'-azobis[2-(2-imidazolin-2-yl)propane] 2,2'-azobis{2-methyl-N-[1,1-bis(hydroxymethyl)-2-hydroxyethyl]propionamide}2,2'-azobis{2-methyl-N-[2-(1-hydroxybutyl)]propionamide} 2,2'-azobis[2-methyl-N-(2-hydroxyethyl)propionamide] and mixtures thereof.

Water-soluble redox initiator systems can also be used as polymerization initiators. Such redox initiator systems comprise at least one peroxide-containing compound in combination with a redox coinitiator, for example reductive sulfur compounds, for example bisulfites, sulfites, thiosulfates, dithionites and tetrathionates of alkali metals and ammonium compounds. Thus, combinations of peroxodisulfates with alkali metal or ammonium hydrogen sulfites can be used, e.g. ammonium peroxodisulfate and ammonium disulfite. The amount of the peroxide-containing compound relative to the redox coinitiator is in the range from 30:1 to 0.05:1.

In combination with the initiators or the redox initiator systems, transition metal catalysts can additionally be used, e.g. salts of iron, cobalt, nickel, copper, vanadium and manganese. Suitable salts are, for example, iron(II) sulfate, cobalt (II) chloride, nickel(II) sulfate, or copper(I) chloride. Based on the monomers, the reductive transition metal salt is used in a concentration of from 0.1 ppm to 1000 ppm. It is thus possible to use combinations of hydrogen peroxide with iron (II) salts, such as, for example, 0.5 to 30% hydrogen peroxide and 0.1 to 500 ppm of Mohrs salt.

Furthermore, redox coinitiators and/or transition metal catalysts can be co-used in combination with the abovementioned initiators, e.g. benzoin, dimethylaniline, ascorbic acid, and complexes of heavy metals, such as copper, cobalt, iron, manganese, nickel and chromium. The amounts of redox coinitiators or transition metal catalysts usually used are about 0.1 to 1000 ppm, based on the amounts of monomers used. Further suitable initiators are described in chapters 20 and 21 of Macromolecules, Vol. 2, 2nd Ed., H. G. Elias, Plenum Press, 1984, New York, to which reference is made here in its entirety. Furthermore, suitable photoinitiators are described in S. P. Pappas, J. Rad. Cur., July 1987, p. 6, to which reference is made here in its entirety.

The amount of the at least one water-soluble initiator used for the polymerization of the monomers is preferably from 0.0001 to 10% by weight, particularly preferably 0.001 to 5% by weight and in particular 0.02 to 3% by weight, based on the total amount of the monomers used.

To adjust the molecular weight, the polymerization can take place in the presence of at least one regulator. Regulators which can be used are the customary compounds known to the person skilled in the art, such as, for example, sulfur compounds, e.g. mercaptoethanol, 2-ethylhexyl thioglycolate, thioglycolic acid or dodecyl mercaptan, and also tribromochloromethane or other compounds which have a regulating effect on the molecular weight of the resulting polymers. A preferred regulator is cystein.

The solution polymerization can be carried out either as a batch process or in the form of a feed method, including monomer feed, stepwise procedure and gradient procedure. Preference is generally given to the feed method in which, if appropriate, some of the polymerization mixture is initially introduced and heated to the polymerization temperature and then the remainder of the polymerization mixture is introduced usually via one or more spatially separate feeds, continuously, stepwise or with overlap of a concentration gradient while maintaining the polymerization of the polymerization zone.

In one embodiment of the invention, the total amount of the monomers a) to d) and, if appropriate, of crosslinker e) and the regulator is initially introduced and the initiator is gradually added to the reaction mixture.

In a further embodiment of the invention, some of monomer a), for example 1 to 50% by weight, preferably 5 to 40% by weight, particularly preferably 10 to 30% by weight, of monomer a), solvent and some of the regulator used if appropriate, for example 1 to 50% by weight, preferably 5 to 40% by weight, particularly preferably 10 to 30% by weight, of the regulator is initially introduced, and the other monomers b), c), if appropriate d), solvent and the remaining regulator in one feed, and solvent and initiator in a second feed are gradually added to the reaction mixture. In this connection, it is advantageous to use solvents both in the initial charge and also in the feeds.

In a further embodiment of the invention, the majority of monomer a), for example more than 50% by weight, preferably more than 60% by weight, further preferably more than 70% by weight, particularly preferably more than 80% by weight and in particular more than 90% by weight, is initially introduced and, if appropriate, heated together with solvent. Then, some of the monomers b) and c), for example up to 50% by weight, preferably up to 40% by weight, particularly preferably up to 30% by weight and in particular up to 20% by weight, of the monomers b) and c) are added to the initial charge, heated if appropriate, and the polymerization is started with the help of initiator. The remainder of the monomers and of the initiator is then gradually metered in.

In a preferred embodiment, the monomers b) and c) are metered in together as a mixture.

The polymerization is preferably carried out largely with exclusion of oxygen. It is preferred to carry out the polymerization under protective gas atmosphere, such as, for example, argon atmosphere or preferably nitrogen atmosphere.

The polymerization can take place in principle at the pH resulting through the monomers used.

Preferably, the pH of the polymerization solution is adjusted to a value of from 5 to 10, further preferably 6 to 9, particularly preferably 6.5 to 8.5.

Preferably, the pH of the initial charge and of the various feeds is adjusted to a value of from 5 to 10, further preferably 6 to 9, particularly preferably 6.5 to 8.5. It is furthermore advantageous to then keep the pH in this range during the polymerization. Of suitability for adjusting the pH before, during or after the polymerization are, in principle, all inorganic or organic bases (and if appropriate acids), in particular those which, apart from possible salt formation, do not react with the monomers. Suitable bases are, for example, alkali metal and alkaline earth metal hydroxides, tertiary amines, such as triethylamine, and also amino alcohols, such as triethanolamine, methyldiethanolamine or dimethylethanolamine. For adjusting the pH, preference is given to using NaOH or at least one tertiary amine, which is selected in particular from N,N-dimethylethanolamine, N-methyldiethanolamine, triethanolamine and mixtures thereof.

To achieve the purest possible polymers with a low residual monomer content, the polymerization (main polymerization) can be followed by an after polymerization step. The after polymerization can take place in the presence of the same initiator system as the main polymerization, or a different initiator system. Preferably, the after polymerization takes place at least at the same temperature as the main polymerization, preferably at a higher temperature than the main polymerization. If desired, the reaction mixture can, after the polymerization or between the first and second polymerization steps, be subjected to stripping with steam or to steam distillation, which is particularly advantageously carried out to eliminate components with an undesired odor.

The monomers used for the polymerization are preferably converted to at least 95%, particularly preferably to at least 99% and in particular to at least 99.9% (degree of polymerization).

The polymers present in solution or dispersed form after the polymerization can be converted to powders by customary drying methods known to the person skilled in the art. Preferred methods are spray drying, spray fluidized-bed drying, drum drying and belt drying. It is likewise possible to use freeze-drying and freeze-concentration. If desired, solvents can also be partially or completely removed by customary methods, e.g. distillation at reduced pressure.

A preferred embodiment of the invention are copolymers which comprise, in copolymerized form,
 a) dimethylaminoethyl methacrylate quaternized with methyl chloride
 b) N-vinylimidazole
 c) vinylpyrrolidone and/or vinylcaprolactam,
 d) if appropriate methacrylic acid.

Another preferred embodiment of the invention are copolymers which comprise, in copolymerized form,
 e) dimethylaminoethyl methacrylate quaternized with dimethyl sulfate
 f) N-vinylimidazole
 g) vinylpyrrolidone and/or vinylcaprolactam,
 h) if appropriate methacrylic acid.

In a particularly preferred embodiment of the invention, for producing the abovementioned copolymers, use is made of monomers a) which are quaternized to at least 90 mol %, preferably to at least 99 mol %.

The invention further provides cosmetic or pharmaceutical compositions comprising
A) at least one copolymer, as defined above, and
B) at least one cosmetically acceptable carrier.

The compositions according to the invention preferably have a cosmetically or pharmaceutically acceptable carrier B) which is chosen from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with mono-, di- or trihydric alcohols that are different from iii),
v) saturated acyclic and cyclic hydrocarbons,
vi) fatty acids,
vii) fatty alcohols,
viii) propellant gases,
and mixtures thereof.

The compositions according to the invention have, for example, an oil or fatty component B) which is selected from: hydrocarbons of low polarity, such as mineral oils; linear saturated hydrocarbons, preferably having more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Preferred oil or fat components B) are selected from paraffin and paraffin oils; vaseline; natural fats and oils, such as castor oil, soya oil, peanut oil, olive oil, sunflower oil, sesame oil, avocado oil, cocoa butter, almond oil, peach kernel oil, ricinus oil, cod-liver oil, pig grease, spermaceti, spermaceti oil, sperm oil, wheat germ oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti, and mixtures of the abovementioned oil or fat components.

Suitable cosmetically and pharmaceutically compatible oil and fat components B) are described in Karl-Heinz Schrader, Grundlagen and Rezepturen der Kosmetika [Fundamentals and formulations of cosmetics], $2^{nd}$ edition, Verlag Huthig, Heidelberg, pp. 319-355, to which reference is made here.

Advantageously, those oils, fats and/or waxes are selected which are described on page 28, line 39 to page 34, line 22 of WO 2006/106140. Reference is hereby made to the content of the specified passage in its entirety.

The content of further oils, fats and waxes is at most 50% by weight, preferably 30% by weight, further preferably at most 20% by weight, based on the total weight of the composition.

Suitable hydrophilic carriers B) are selected from water, mono-, di- or polyhydric alcohols having preferably 1 to 8 carbon atoms, such as ethanol, n-propanol, isopropanol, propylene glycol, glycerol, sorbitol, etc.

The cosmetic compositions according to the invention may be skin cosmetic, hair cosmetic, dermatological, hygiene or pharmaceutical compositions. On account of their film-forming properties, the above-described copolymers and polyelectrolyte complexes are suitable in particular as additives for hair and skin cosmetics.

Preferably, the compositions according to the invention are in the form of a gel, foam, spray, ointment, cream, emulsion, suspension, lotion, milk or paste. If desired, liposomes or microspheres can also be used.

The cosmetically or pharmaceutically active compositions according to the invention can additionally comprise cosmetically and/or dermatologically active ingredients, as well as auxiliaries.

Preferably, the cosmetic compositions according to the invention comprise at least one copolymer A) as defined above, at least one carrier B) as defined above and at least one constituent different therefrom, which is selected from cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, consistency regulators, humectants, refatting agents, collagen, protein hydrolyzates, lipids, antioxidants, antifoams, antistats, emollients and softeners.

The cosmetic compositions according to the invention can be present as aqueous or aqueous-alcoholic solutions, O/W and W/O emulsions, hydrodispersion formulations, solids-stabilized formulations, stick formulations, PIT formulations, in the form of creams, foams, sprays (pump spray or aerosol), gels, gel sprays, lotions, oils, oil gels or mousse and accordingly can be formulated with customary further auxiliaries.

Particularly preferred cosmetic compositions for the purposes of the present invention are shampoos and haircare compositions. The invention accordingly also relates to compositions for the cleansing and/or care of the hair.

In particular, the invention relates to haircare compositions selected from the group consisting of pretreatment compositions, hair rinses, hair conditioners, hair balms, leave-on hair treatments, rinse-off hair treatments, hair tonics, pomades, styling creams, styling lotions, styling gels, end fluids, hot-oil treatments and foam treatments.

Furthermore, the invention relates to cosmetic compositions which are selected from gel creams, hydroformulations, stick formulations, cosmetic oils and oil gels, mascara, self-tanning compositions, facecare compositions, bodycare compositions, aftersun preparations, hair-shaping compositions and hair-setting compositions.

Further cosmetic compositions according to the invention are skin cosmetic compositions, in particular those for skincare. These are present in particular as W/O or O/W skin creams, day and night creams, eye creams, face creams, antiwrinkle creams, mimic creams, moisturizing creams, bleach creams, vitamin creams, skin lotions, care lotions and moisturizing lotions.

Furthermore, the polymer combinations according to the invention are suitable as ingredients for skin cosmetic preparations such as face tonics, face masks, deodorants and other cosmetic lotions and for use in decorative cosmetics, for example as concealing stick, stage make-up, in mascara and eye shadows, lipsticks, kohl pencils, eyeliners, make-up, foundations, blushers and powders and eyebrow pencils.

Furthermore, the compositions according to the invention can be used in nose strips for pore cleansing, in antiacne compositions, repellents, shaving compositions, hair removal compositions, personal hygiene compositions, footcare compositions, and also in babycare.

Further preferred compositions according to the invention are washing, showering and bathing preparations which comprise the copolymers according to the invention. For the purposes of this invention, washing, showering and bathing preparations are understood as meaning soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and gels, foam baths, oil baths and scrub preparations, shaving foams, lotions and creams.

Suitable further ingredients for these washing, showering and bathing preparations according to the invention are described below.

Besides the copolymers according to the invention, the compositions comprise further cosmetically acceptable additives, such as, for example, emulsifiers and coemulsifiers, solvents, surfactants, oil bodies, preservatives, perfume oils, cosmetic care and active ingredients, such as AHA acids, fruit acids, ceramides, phytantriol, collagen, vitamins and provitamins, for example vitamin A, E and C, retinol, bisabolol, panthenol, natural and synthetic photoprotective agents, natural substances, opacifiers, solubility promoters, repellents, bleaches, colorants, tinting agents, tanning agents (e.g. dihydroxyacetone), micropigments, such as titanium oxide or zinc oxide, super fatting agents, pearlescent waxes, consistency regulators, thickeners, solubilizers, complexing agents, fats, waxes, silicone compounds, hydrotropes, dyes, stabilizers, pH regulators, reflectors, proteins and protein hydrolyzates (e.g. wheat, almond or pea proteins), ceramide, protein hydrolyzates, salts, gel formers, consistency regulators, silicones, humectants (e.g. 1,2-pentanediol), refatting agents, UV photoprotective filters and further customary additives. Furthermore, to establish the properties desired in each case, it is in particular also possible for further polymers to be present.

The cosmetic compositions according to the invention comprise the copolymers according to the invention in an amount of from 0.01 to 10% by weight, preferably 0.05 to 5% by weight, particularly preferably 0.1 to 1.5% by weight, based on the weight of the composition.

In a preferred embodiment of the invention, the inventive washing, showering and bathing preparations, and shampoos and haircare compositions furthermore comprise at least one surfactant.

In a further preferred embodiment of the invention, besides the polymers, the shampoos and haircare compositions according to the invention furthermore comprise at least one oil and/or fatty phase and a surfactant.

Surfactants

Surfactants which can be used are anionic, cationic, nonionic and/or amphoteric surfactants.

Advantageous washing-active anionic surfactants for the purposes of the present invention are
- acylamino acids and salts thereof, such as acyl glutamates, in particular sodium acyl glutamate
- sarcosinates, for example myristoyl sarcosine, TEA lauroyl sarcosinate, sodium lauroyl sarcosinate and sodium cocoyl sarcosinate, sulfonic acids and salts thereof, such as
- acyl isethionates, for example sodium or ammonium cocoyl isethionate
- sulfosuccinates, for example dioctyl sodium sulfosuccinate, disodium laureth sulfosuccinate, disodium lauryl sulfosuccinate and disodium undecylenamido MEA sulfosuccinate, disodium PEG-5 lauryl citrate sulfosuccinate and derivatives,
- alkyl ether sulfates, for example sodium, ammonium, magnesium, MIPA, TIPA laureth sulfates, sodium myreth sulfate and sodium $C_{12-13}$ pareth sulfate,
- alkyl ether sulfonates, for example sodium C12-15 pareth-15 sulfonate
- alkyl sulfates, for example sodium, ammonium and TEA lauryl sulfate.

Further advantageous anionic surfactants are
- taurates, for example sodium lauroyl taurate and sodium methyl cocoyl taurate,
- ether carboxylic acids, for example sodium laureth-13 carboxylate and sodium PEG-6 cocamide carboxylate, sodium PEG-7 olive oil carboxylate
- phosphoric acid esters and salts, such as, for example, DEA oleth-10 phosphate and dilaureth-4 phosphate, alkyl sulfonates, for example, sodium coconut monoglyceride sulfate, sodium $C_{12\text{-}14}$ olefinsulfonate, sodium lauryl sulfoacetate and magnesium PEG-3 cocamide sulfate, acyl glutamates, such as di-TEA palmitoyl aspartate and sodium caprylic/capric glutamate, acyl peptides, for example palmitoyl hydrolyzed milk protein, sodium cocoyl hydrolyzed soya protein and sodium/potassium cocoyl hydrolyzed collagen, and also carboxylic acids and derivatives, such as, for example, lauric acid, aluminum stearate, magnesium alkanolate and zinc undecylenate, ester carboxylic acids, for example, calcium stearoyl lactylate, laureth-6 citrate and sodium PEG-4 lauramide carboxylate alkylarylsulfonates.

Advantageous washing-active cationic surfactants for the purposes of the present invention are quaternary surfactants. Quaternary surfactants comprise at least one N atom which is covalently bonded to 4 alkyl or aryl groups. For example, alkylbetaine, alkylamidopropylbetaine and alkylamidopropylhydroxysultaine are advantageous. Further advantageous cationic surfactants for the purposes of the present invention are also alkylamines,
alkylimidazoles and
ethoxylated amines and in particular salts thereof.

Advantageous washing-active amphoteric surfactants for the purposes of the present invention are acyl/dialkylethylenediamines, for example sodium acyl amphoacetate, disodium acyl amphodipropionate, disodium alkyl amphodiacetate, sodium acyl amphohydroxypropylsulfonate, disodium acyl amphodiacetate, sodium acyl amphopropionate, and N-coconut fatty acid amidoethyl N-hydroxyethylglycinate sodium salts.

Further advantageous amphoteric surfactants are N-alkylamino acids, for example aminopropylalkylglutamide, alkylaminopropionic acid, sodium alkylimidodipropionate and lauroamphocarboxyglycinate.

Advantageous washing-active nonionic surfactants for the purposes of the present invention are alkanolamides, such as cocamides MEA/DEA/MIPA,
esters which are formed by esterification of carboxylic acids with ethylene oxide, glycerol, sorbitan or other alcohols,
ethers, for example ethoxylated alcohols, ethoxylated lanolin, ethoxylated polysiloxanes, propoxylated POE ethers, alkyl polyglycosides, such as lauryl glucoside, decyl glycoside and cocoglycoside, glycosides with a HLB value of at least 20 (e.g. Belsil®SPG 128V (Wacker)).

Further advantageous nonionic surfactants are alcohols and amine oxides, such as cocoamidopropylamine oxide.

Preferred anionic, amphoteric and nonionic shampoo surfactants are specified, for example, in "Kosmetik and Hygiene von Kopf bis Fuβ" [Cosmetics and Hygiene from Head to Toe], Ed. W. Umbach, $3^{rd}$ edition, Wiley-VCH, 2004, pp. 131-134, to which reference is made at this point in its entirety.

Among the alkyl ether sulfates, sodium alkyl ether sulfates based on di- or triethoxylated lauryl and myristyl alcohol in particular are preferred. They are clearly superior to the alkyl sulfates with regard to insensitivity toward water hardness, ability to be thickened, low-temperature solubility and, in particular, skin and mucosa compatibility. They can also be used as sole washing raw materials for shampoos. Lauryl ether sulfate has better foam properties than myristyl ether sulfate, but is inferior to this as regards mildness.

Alkyl ether carboxylates belong to the mildest surfactants overall, but exhibit poor foaming and viscosity behavior. They are often used in combination with alkyl ether sulfates and amphoteric surfactants in hair washing compositions.

Sulfosuccinic acid esters (sulfosuccinates) are mild and readily foaming surfactants, but, on account of their poor ability to be thickened, are preferably only used together with other anionic and amphoteric surfactants and, on account of their low hydrolysis stability, are preferably only used in neutral and well buffered products.

Amidopropylbetaines as sole washing raw materials are unimportant in practice since their foaming behavior and also their ability to be thickened are only moderate. On the other hand, these surfactants have excellent skin and eye mucosa compatibility. In combination with anionic surfactants, their mildness can be synergistically improved. Preference is given to the use of cocamidopropylbetaine.

Amphoacetates/amphodiacetates have, as amphoteric surfactants, very good skin and mucosa compatibility and can have a hair-conditioning effect and/or enhance the care effect of additives. Similarly to the betaines, they are used for the optimization of alkyl ether sulfate formulations. Sodium cocoamphoacetate and disodium cocoamphodiacetate are most preferred.

Alkyl polyglycosides are nonionic washing raw materials. They are mild, have good universal properties, but are weakly foaming. For this reason, they are preferably used in combinations with anionic surfactants.

Sorbitan esters are likewise types of nonionic washing raw materials. On account of their excellent mildness, they are preferably employed for use in baby shampoos.

Being weak foamers, they are preferably used in combination with anionic surfactants. It is advantageous to select the washing-active surfactant or surfactants from the group of surfactants which have a HLB value of more than 25, those which have a HLB value of more than 35 being particularly advantageous.

According to the invention, it is advantageous if one or more of these surfactants is used in a concentration of from 1 to 30% by weight, preferably in a concentration of from 5 to 25% by weight and very particularly preferably in a concentration of from 10 to 20% by weight, in each case based on the total weight of the composition.

Polysorbates

As washing-active agents, polysorbates can also advantageously be incorporated into the compositions according to the invention.

Polysorbates advantageous for the purposes of the invention are, for example, polyoxyethylene(20) sorbitan monolaurate (Tween®20, CAS No. 9005-64-5)

polyoxyethylene(4) sorbitan monolaurate (Tween®21, CAS No. 9005-64-5)

polyoxyethylene(4) sorbitan monostearate (Tween®61, CAS No. 9005-67-8)

polyoxyethylene(20) sorbitan tristearate Tween®65, CAS No. 9005-71-4)

polyoxyethylene(20) sorbitan monooleate (Tween®80, CAS No. 9005-65-6)

polyoxyethylene(5) sorbitan monooleate (Tween®81, CAS No. 9005-65-5)

polyoxyethylene(20) sorbitan trioleate (Tween®85, CAS No. 9005-70-3).

Polyoxyethylene(20) sorbitan monopalmitate (Tween®40, CAS No. 9005-66-7) and polyoxyethylene(20) sorbitan monostearate (Tween®60, CAS No. 9005-67-8) are particularly advantageous.

The polysorbates are advantageously used in a concentration of from 0.1 to 5% by weight and in particular in a concentration of from 1.5 to 2.5% by weight, based on the total weight of the composition, individually or as a mixture of two or more polysorbates.

Further Conditioners

If desired, in addition to the copolymers according to the invention, further conditioners selected for the cosmetic compositions according to the invention are preferably those conditioners which are described on page 34, line 24 to page 37, line 10 of WO 2006/106140. Reference is hereby made to the content of the specified passage in its entirety.

Rheology Modifiers

Suitable rheology modifiers are primarily thickeners. Thickeners Suitable for shampoos and haircare compositions are given in "Kosmetik and Hygiene von Kopf bis Fuß" [Cosmetics and Hygiene from Head to Toe], Ed. W. Umbach, $3^{rd}$ edition, Wiley-VCH, 2004, pp. 235-236, to which reference is made at this point in its entirety.

Suitable thickeners for the cosmetic compositions according to the invention are described, for example, also on page 37, line 12 to page 38, line 8 of WO 2006/106140. Reference is hereby made to the content of the specified passage in its entirety.

Preservatives

The cosmetic compositions according to the invention can also comprise preservatives. Compositions with high water contents have to be reliably protected against the buildup of germs. Suitable preservatives for the cosmetic compositions according to the invention are described, for example, on page 38, line 10 to page 39, line 18 of WO 2006/106140. Reference is hereby made to the content of the specified passage in its entirety.

Complexing agents: since the raw materials and also the shampoos themselves are produced primarily in steel apparatuses, the end products can comprise iron (ions) in trace amounts. In order to prevent these impurities adversely affecting the product quality through reactions with dyes and perfume oil constituents, complexing agents such as salts of ethylenediaminetetraacetic acid, of nitrilotriacetic acid, of iminodisuccinic acid or phosphates are added.

UV photoprotective filters: in order to stabilize the ingredients present in the compositions according to the invention, such as, for example, dyes and perfume oils, against changes due to UV light, UV photoprotective filters, such as, for example, benzophenone derivatives, can be incorporated. Suitable UV photoprotective filters for the cosmetic compositions according to the invention are described, for example, on page 39, line 20 to page 41, line 10 of WO 2006/106140. Reference is hereby made to the content of the specified passage in its entirety.

Antioxidants: a content of antioxidants in the compositions according to the invention is generally preferred. According to the invention, antioxidants which can be used are all antioxidants customary or suitable for cosmetic applications. Suitable antioxidants for the cosmetic compositions according to the invention are described, for example, on page 41, line 12 to page 42, line 33 of WO 2006/106140. Reference is hereby made to the content of the specified passage in its entirety.

Buffers: buffers ensure the pH stability of the compositions. Citrate, lactate and phosphate buffers are primarily used.

Solubility promoters: they are used in order to bring care oils or perfume oils clearly into solution and also to keep them clearly in solution at low temperature. The most common solubility promoters are ethoxylated nonionic surfactants, for example hydrogenated and ethoxylated ricinus oils.

Antimicrobial agents: furthermore, antimicrobial agents can also be used. These include, in general, all suitable preservatives with specific action against gram-positive bacteria, e.g. triclosan (2,4,4'-trichloro-2'-hydroxy diphenyl ether), chlorhexidine (1,1'-hexamethylenebis[5-(4-chlorophenyl) biguanide), and TTC (3,4,4'-trichlorocarbanilide). Quaternary ammonium compounds are in principle likewise suitable and are preferably used for disinfectant soaps and washing lotions. Numerous fragrances also have antimicrobial properties. A large number of essential oils or their characteristic ingredients, such as, for example, clove oil (eugenol), mint oil (menthol) or thyme oil (thymol), also exhibit marked antimicrobial effectiveness.

The antibacterially effective substances are generally used in concentrations of from about 0.1 to 0.3% by weight.

Dispersants: if insoluble active ingredients, e.g. antidandruff active ingredients or silicone oils, are to be dispersed or kept permanently in suspension in the compositions according to the invention, dispersants and thickeners, such as, for example, magnesium-aluminum silicates, bentonites, fatty acyl derivatives, polyvinylpyrrolidone or hydrocolloids, e.g. xanthan gum or carbomers, have to be used.

According to the invention, preservatives are present in a total concentration of at most 2% by weight, preferably at most 1.5% by weight and particularly preferably at most 1% by weight, based on the total weight of the composition.

Apart from the abovementioned substances, the compositions can, if appropriate, comprise the additives customary in cosmetics, for example perfume, dyes, refatting agents, complexing and sequestering agents, pearlizing agents, plant extracts, vitamins, active ingredients, pigments which have a coloring effect, softening, moisturizing and/or humectant substances, or other customary constituents of a cosmetic or dermatological formulation, such as alcohols, polyols, polymers, organic acids for adjusting the pH, foam stabilizers, electrolytes, organic solvents or silicone derivatives.

With regard to the specified further ingredients known to the person skilled in the art for the compositions, reference may be made to "Kosmetik and Hygiene von Kopf bis Fuß" [Cosmetics and Hygiene from Head to Toe], Ed. W. Umbach, $3^{rd}$ edition, Wiley-VCH, 2004, pp. 123-128, to which reference is made at this point in its entirety.

The polymers according to the invention are suitable for enhancing or for increasing the deposition amount and rate, and also the residence time of further active ingredients, such as, for example; silicones or UV photoprotective filters, on the skin and/or the hair. Substances or compositions which have such effects are also referred to as depositioning aids.

U.S. Pat. No. 6,998,113 describes rinse-off preparations which lead to the skin treated therewith being effectively protected from UV radiation. Some of the preparations described therein comprise cationic polymers. For the purposes of the present invention, the copolymers according to the invention can also be used in the preparations of U.S. Pat. No. 6,998,113. In particular, the copolymers according to the invention can be used for the purpose specified by U.S. Pat. No. 6,998,113 in sunscreen, washing and bathing preparations. Reference is hereby made to the disclosure of U.S. Pat. No. 6,998,113 in its entirety.

Suitable silicones are described, for example, in U.S. Pat. No. 5,935,561, column 13, 1.64 to column 18, 1.61, to which reference is hereby made in its entirety.

By way of representation, mention may be made of:
dimethicones
polyalkyl- or polyarylsiloxanes (U.S. Pat. No. 5,935,561, column 13, formula I)
alkylamino-substituted silicones (U.S. Pat. No. 5,935,561, column 14, formula II (amodimethicons))
cationic silicones (U.S. Pat. No. 5,935,561, columns 14 and 15, formula III)
trimethylsilylamodimethicones (U.S. Pat. No. 5,935,561, column 15, formula IV)
silicones as in U.S. Pat. No. 5,935,561, column 15, formula V
cyclic polysiloxanes as in U.S. Pat. No. 5,935,561, column 16, formula VI
ethoxylated glycerol fatty acid esters The compositions according to the invention, such as shampoos and haircare compositions, comprise, if appropriate, ethoxylated oils selected from the group of ethoxylated glycerol fatty acid esters, particularly preferably PEG-10 olive oil glycerides, PEG-11 avocado oil glycerides, PEG-11 cocoa butter glycerides, PEG-13 sunflower oil glycerides, PEG-15 glycerylisostearate, PEG-9 coconut fatty acid glycerides, PEG-54 hydrogenated ricinus oil, PEG-7 hydrogenated ricinus oil, PEG-60 hydrogenated ricinus oil, jojoba oil ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 ricinus oil, olive oil PEG-7 ester, PEG-6 caprylic acid/capric acid glycerides, PEG-10 olive oil glycerides, PEG-13 sunflower oil glycerides, PEG-7 hydrogenated ricinus oil, hydrogenated palm kernel oil glyceride PEG-6 ester, PEG-20 corn oil glycerides, PEG-18 glyceryl oleate cocoate, PEG-40 hydrogenated ricinus oil, PEG-40 ricinus oil, PEG-60 hydrogenated ricinus oil, PEG-60 corn oil glycerides, PEG-54 hydrogenated ricinus oil, PEG-45 palm kernel oil glycerides, PEG-80 glyceryl cocoate, PEG-60 almond oil glycerides, PEG-60 evening primrose glycerides, PEG-200 hydrogenated glycerylpalmate, PEG-90 glyceryl isostearate.

Preferred ethoxylated oils are PEG-7 glyceryl cocoate, PEG-9 coconut glycerides, PEG-40 hydrogenated ricinus oil, PEG-200 hydrogenated glycerylpalmate. Ethoxylated glycerol fatty acid esters are used in aqueous cleaning formulations for various purposes. Glycerol fatty acid esters with a degree of ethoxylation of about 30-50 serve as solubility promoters for nonpolar substances such as perfume oils. Highly ethoxylated glycerol fatty acid esters are used as thickeners.

Active Ingredients

Highly diverse active ingredients of varying solubility can be incorporated homogeneously into the compositions according to the invention. Advantageous active ingredients in the cosmetic compositions according to the invention are described, for example, on page 44, line 24 to page 49, line 39 of WO 2006/106140. Reference is hereby made to the content of the specified passage in its entirety.

UV Photoprotective Agents

In a preferred embodiment, the compositions according to the invention comprise UV photoprotective agents for protecting the skin and/or the hair. Suitable UV photoprotective agents are described in detail in WO 2006/106114, p. 24, l.4 to p. 27, l.27, to which reference is hereby made in its entirety.

The compositions advantageously comprise substances which absorb UV radiation in the UVB region and substances which absorb UV radiation in the UVA region, the total amount of the filter substances being, for example, 0.1 to 30% by weight, preferably 0.5 to 20% by weight, in particular 1 to 15% by weight, based on the total weight of the compositions, in order to provide cosmetic compositions which protect the skin from the entire range of ultraviolet radiation.

The majority of the photoprotective agents in the cosmetic or dermatological compositions serving to protect the human epidermis consists of compounds which absorb UV light in the UV-B region. For example, the fraction of the UV-A absorbers to be used according to the invention is 10 to 90% by weight, preferably 20 to 50% by weight, based on the total amount of substances absorbing UV-B and UV-A.

Pearlescent Waxes

Suitable pearlescent waxes for the cosmetic compositions according to the invention are described, for example, on page 50, line 1 to line 16 of WO 2006/106140. Reference is hereby made to the content of the specified passage in its entirety.

The compositions according to the invention can furthermore comprise glitter substances and/or other effect substances (e.g. color streaks).

Emulsifiers

In a preferred embodiment of the invention, the cosmetic compositions according to the invention are in the form of emulsions. Such emulsions are prepared by known methods. Suitable emulsifiers for the emulsions according to the invention are described, for example, on page 50, line 18 to page 53, line 4 of WO 2006/106140. Reference is hereby made to the content of the specified passage in its entirety.

Perfume Oils

If perfume oils are to be added to the cosmetic compositions according to the invention, then suitable perfume oils are described, for example, on page 53, line 10 to page 54, line 3 of WO 2006/106140. Reference is hereby made to the content of the specified passage in its entirety.

Pigments

If appropriate, the cosmetic compositions according to the invention furthermore comprise pigments. The pigments are present in the product mostly in undissolved form and may be present in an amount of from 0.01 to 25% by weight, particularly preferably from 5 to 15% by weight. The preferred particle size is 1 to 200 µm, in particular 3 to 150 µm, particularly preferably 10 to 100 µm.

Suitable pigments for the compositions according to the invention are described, for example on page 54, line 5 to page 55, line 19 of WO 2006/106140. Reference is hereby made to the content of the specified passage in its entirety.

Polymers

In a preferred embodiment, apart from the polymer produced by the method according to the invention, the cosmetic compositions according to the invention comprise further polymers.

Suitable additional polymers for the compositions according to the invention are described, for example, on page 55, line 21 to page 63, line 2 of WO 2006/106140. Reference is hereby made to the content of the specified passage in its entirety.

Shampoo Types

A preferred embodiment of the invention are hair shampoos comprising the copolymers according to the invention. Additional requirements are, if appropriate, placed on shampoos according to hair quality or scalp problem. The mode of action of the preferred shampoo types with the most important additional effects or most important special objectives is described below.

According to the invention, preference is given, for example, to shampoos for normal or rapidly greasing or damaged hair, antidandruff shampoos, baby shampoos and two-in-one shampoos (i.e. shampoo and conditioner in one).

Shampoos according to the invention for normal hair: hair washing should free hair and scalp from the skin sebum formed in sebaceous glands, the inorganic salts emerging from sweat glands with water, amino acids, urea and lactic acid, shed skin particles, environmental dirt, odors and, if appropriate, residues of hair cosmetic treatments. Normal hair means short to shoulder-length hair which is only slightly damaged. Accordingly, the fraction of conditioning auxiliaries should be optimized to this hair type. Shampoos according to the invention for rapidly greasing hair increased sebum production by the sebaceous glands on the scalp leads just 1-2 days after hair washing to a straggly, unkept hairstyle. Oil- and wax-like skin sebum constituents weigh down the hair and reduce the friction from hair to hair and thus reduce the hairstyle hold. The actual hair cosmetic problem in the case of rapidly greasing hair is thus the premature collapse of voluminous hairstyles. In order to avoid this, it is necessary to prevent the hair surface becoming weighed down and too smooth and supple. This is preferably achieved through the surfactant base of highly cleaning washing raw materials that are characterized by particularly low substantivity. Additional care substances which would add to the skin sebum, such as refatting substances, are used in shampoos for rapidly greasing hair only with the greatest of care, if at all. Volumizing shampoos according to the invention for fine hair can be formulated comparably.

Shampoos according to the invention for dry, stripped (damaged) hair the structure of the hair is changed in the course of hair growth by mechanical influences such as combing, brushing and primarily back-combing (combing against the direction of growth), by the effect of UV radiation and visible light and by cosmetic treatments, such as permanent waves, bleaching or coloring. The flake layer of the hair has an increasingly stripped appearance from root to the end; in extreme cases, it is completely worn away at the end, and the hair ends are split (split ends). Damaged hair can in principle no longer be returned to the state of healthy hair regrowth. However, it is possible to come very close to this ideal state as regards feel, shine and combability by using shampoos according to the invention with, if appropriate, high fractions of care substances (conditioners).

An even better hair conditioning effect than with a shampoo is achieved with a haircare composition according to the invention, for example in the form of a rinse or cure treatment after hair washing. Rinses or cures for hair which comprise copolymers according to the invention are likewise in accordance with the invention.

2-in-1 shampoos according to the invention are particularly high-care shampoos in which, as a result of the design as "shampoo and conditioner in one" the additional care benefit is placed equally alongside the basic cleaning benefit. 2-in-1 compositions according to the invention comprise increased amounts of conditioners.

Antidandruff shampoos: compared with antidandruff hair tonics, antidandruff shampoos according to the invention have the advantage that they not only reduce the formation of new visible flakes through appropriate active ingredients against dandruff attack and prevent such formation upon long-term application, but also remove flakes already shed with the hair washing. However, after rinsing out the wash liquor, only a small, but adequate amount of the active ingredients remains on the scalp and hair. There are various antidandruff active ingredients which can be incorporated into the shampoo compositions according to the invention, such as, for example, zinc pyrithion, ketoconazole, elubiol, clotrimazole, climbazole or piroctone olamine. Additionally, these substances have a normalizing effect on shedding.

The basis of antidandruff shampoos corresponds primarily to the formulation of shampoos for normal hair with a good cleaning effect.

Baby shampoos: in a preferred embodiment of the invention, the shampoo preparations according to the invention are baby shampoos. These are optimally skin- and mucosa-compatible. Combinations of washing raw materials with very good skin compatibility form the basis of these shampoos. Additional substances for further improving the skin and mucosa compatibility and the care properties are advantageously added, such as, for example, nonionic surfactants, protein hydrolyzates and panthenol or bisabolol. All of the required raw materials and auxiliaries, such as preservatives, perfume oils, dyes etc., are selected from the aspect of high compatibility and mildness.

Shampoos for dry scalp: in a further preferred embodiment of the invention, the shampoo preparations according to the invention are shampoos for dry scalp. The primary aim of these shampoos is to prevent the scalp from drying out since dry scalp can lead to irritation, reddening and inflammation. As also in the case of the baby shampoos, combinations of washing raw materials with very good skin compatibility form the basis of these shampoos. Additionally, if appropriate, refatting agents and humectants, such as, for example, glycerol or urea, can be used.

The shampoo compositions according to the invention can also be present as shampoo concentrates with increased surfactant contents of 20-30% by weight. They are based on special washing raw material combinations and consistency regulators which ensure good spreadability and the spontaneous foaming ability even of a small application amount. A particular advantage is, for example, the possibility of achieving the productivity of 200 ml of shampoo with a 100 ml bottle.

Supply Form

It is advantageous if the compositions according to the invention are stored in a bottle or squeezable bottle and are applied from this. Accordingly, bottles or squeezable bottles which comprise a composition according to the invention are also in accordance with the invention.

The copolymers according to the invention, as defined above, can preferably be used in shampoo formulations in particular as conditioners. Preferred shampoo formulations comprise a) 0.05 to 10% by weight of at least one copolymer according to the invention,
b) 25 to 94.95% by weight of water,
c) 5 to 50% by weight of surfactants,
c) 0 to 5% by weight of a further conditioner,
d) 0 to 10% by weight of further cosmetic constituents.

All anionic, neutral, amphoteric or cationic surfactants customarily used in shampoos can be used in the shampoo formulations. Suitable surfactants have been specified above.

Soaps and Syndets

Further compositions according to the invention which comprise the copolymers according to the invention are, for example, soaps and syndets.

Soap is formed in the reaction of a (neutral) fat or fatty acids obtained therefrom or fatty acid methyl ester with sodium hydroxide or potassium hydroxide (saponification). Soap is chemically the alkali metal salt of fatty acids in the composition. The neutral fats usually used in the manufacture of soap are beef tallow or palm oil in a mixture with coconut oil or palm kernel oil and—more rarely—other natural oils or fats, the quality of the starting fats being highly influential on the quality of the soap obtained therefrom.

Of importance for selecting the fatty components is the distribution of the chain lengths of the corresponding fatty acids. Normally, especially C12-C18-fatty acids are in demand. Since laurate soap foams particularly well, lauric-rich coconut oil or similarly formulated palm kernel oil are usually used in relatively high fractions (up to 50% of the neutral fatty mixture) for soaps for which a large amount of foam during use is desired. The sodium salts of the specified fatty acid mixtures are solid, whereas the potassium salts are soft and pasty. For this reason, the hydroxide solution component used for producing solid soaps is preferably sodium hydroxide solution, and for liquid-pasty soaps is preferably potassium hydroxide solution. During the saponification, the ratio of hydroxide solution to fatty acid is selected so that, at most, a minimum excess of hydroxide solution (max. 0.05%) is present in the finished soap bar.

The soaps usually include toilet, curd, transparent, luxury, cream, freshening/deodorant, baby, skin protection, abrasive, floating and liquid soaps and also washing pastes and soap leaves.

Besides the copolymers according to the invention, soaps according to the invention advantageously furthermore comprise antioxidants, complexing agents and humectants, and, if appropriate, fragrances, dyes and further cosmetically acceptable ingredients. Such further suitable ingredients are specified above.

Syndets (synthetic detergents) are alternatives to conventional soaps which have certain advantages as a result of the varying composition compared to soap, whereas soap more likely has disadvantages.

Syndets comprise, as foam and cleaning components, washing-active substances (surfactants) which are obtained by chemical synthesis. By contrast, soaps are—as described—salts of naturally occurring fatty acids. For syndets, skin-mild, readily biodegradable surfactants are used, preferably fatty acid isethionates (sodium cocoyl isethionate), sulfosuccinic acid half-esters (disodium lauryl sulfosuccinate), alkyl polyglucosides (decyl glucoside), amphoteric surfactants (e.g. sodium cocoamphoacetate). In addition, monoglyceride sulfate and ether carboxylates sometimes play a role. Fatty alcohol sulfate (e.g. sodium lauryl sulfate) has largely lost its former significance as base surfactant for syndets. The base surfactants are combined with builder substances, refatting agents and further additives to give formulations which can be processed by customary soap technology and produce bars which behave as far as possible "soap-like", but without the mentioned disadvantages of soap. They foam at every water hardness and have a very good cleaning power. Their pH can be adjusted within a wide range (mostly between 4 and 8).

On account of the more intensive cleaning/degreasing power of the base surfactants, the surfactant fraction in the syndet is usually significantly lower, the fraction of super fatting agents is significantly higher than in soaps without the foaming ability being reduced. Syndets are recommended specifically for the cleansing of sensitive skin, of youthful-blemished skin and for face washing.

Alongside the (soap-free) syndets is also found the market segment of half- or combars (derived from combination bar). These are bars which comprise both soap and syndet surfactants. Combars comprise 10 to 80% by weight of soap. They represent a compromise between soaps and syndets for the criteria of costs, foaming ability, skin feel and compatibility. When washing with a combar, a pH of from about 7 to 9 is established, depending on its soap fraction.

As regards possible formulations for soaps and syndets known to the person skilled in the art, reference may be made to "Kosmetik und Hygiene von Kopf bis Fuß" [Cosmetics and Hygiene from Head to Toe], Ed. W. Umbach, $3^{rd}$ edition, Wiley-VCH, 2004, pp. 112-122, to which reference is made at this point in its entirety.

Shower Bath and Bathing Products

As regards specific compositions for shower bath and bathing products or washing lotions, reference may be made to "Kosmetik und Hygiene von Kopf bis Fuß" [Cosmetics and Hygiene from Head to Toe], Ed. W. Umbach, $3^{rd}$ edition, Wiley-VCH, 2004, pp. 128-134, to which reference is made at this point in its entirety.

The invention further provides the use of a copolymer according to the invention as auxiliary in pharmacy, preferably as or in (a) coating composition(s) for solid drug forms, for modifying theological properties, as surface-active compound, as or in (an) adhesive(s), and as or in (a) coating composition(s) for the textile, paper, printing and leather industries.

EXAMPLES

Preparation Examples

| Abbreviations: | |
|---|---|
| CD: | completely demineralized |
| TMAEMC: | 2-trimethylammonium ethyl methacrylate chloride |
| Quat311 | 2-trimethylammonium ethyl methacrylate ethyl sulfate |
| VI: | N-vinylimidazole |
| VP: | N-vinylpyrrolidone |
| MAA: | methacrylic acid |
| min: | minute(s) |
| h: | hour(s) |
| mon. | months |
| AI: | active ingredient; e.g. pure polymer without solvents or other additives |

Unless noted otherwise, the % data below are % by weight.

The details relating to the monomer compositions such as, for example "75/12.5/12.5" give the weight ratios of the monomers used for the polymerization.

Example P1

TMAEMC/VI/VP 75/12.5/12.5

85.00 g of CD water, 28.00 g of 2-trimethylammonium ethyl methacrylate chloride (75% strength by weight) and 0.60 g of mercaptoethanol were initially introduced and adjusted to pH=8.5 with 50% strength by weight NaOH solution. The initial charge was gassed with nitrogen and heated to 57° C. with stirring. Then, 1.98 g of feed 2 were added batchwise and the mixture was polymerized for 15 min. Feed 1 was metered in over the course of 5 h, while the remainder of feed 2 (26.37 g) was metered in over the course of 5.5 h. When the feed was complete, the reaction mixture was heated to 70° C. and afterpolymerized for 1 h. After cooling, the polymer solution was preserved with 1.90 g of Phenonip.

Feed 1:

122.00 g of 2-trimethylammonium ethyl methacrylate chloride (75% strength by weight), 70.00 g of CD water, 3.90 g of mercaptoethanol, 18.75 g of N-vinylimidazole, 18.75 g of N-vinylpyrrolidone, adjusted to pH 8.5 with 50% strength by weight NaOH.

Feed 2:
  26.25 g of CD water, 2.10 g of Wako®V 50

Example P1b

TMAEMC/VI/VP 75/12.5/12.5

85.00 g of CD water, 28.00 g of 2-trimethylammonium ethyl methacrylate chloride (75% strength by weight) and 0.60 g of mercaptoethanol were initially introduced and adjusted to pH=8.5 with 50% strength by weight NaOH solution. The initial charge was gassed with nitrogen and heated to 57° C. with stirring. Then, 1.98 g of feed 3 were added batchwise and the mixture was polymerized for 15 min. Feed 1 and feed 2 were metered in over the course of 5 hours. The remainder of feed 3 was metered in over the course of 5.5 hours. When the feed was complete, the reaction mixture was heated to 70° C. and afterpolymerized for 1 hour. After cooling, the polymer solution was preserved with 1.90 g of Phenonip.
Feed 1:
  122.00 g of 2-trimethylammonium ethyl methacrylate chloride (75% strength by weight), 70.00 g of CD water, adjusted to pH=8.5 with 50% strength by weight NaOH solution.
Feed 2:
  18.75 g of N-vinylimidazole, 18.75 g of N-vinylpyrrolidone, 1.65 g of mercaptoethanol
Feed 3:
  2.70 g of Wako®V50, 26.25 g of CD water Example C1

TMAEMC/VP 75/25 (comparative experiment)

85.00 g of CD water, 28.00 g of 2-trimethylammonium ethyl methacrylate chloride (75% strength by weight) and 0.60 g of mercaptoethanol were initially introduced and adjusted to pH=8.5 with 50% strength by weight NaOH solution. The initial charge was gassed with nitrogen and heated to 57° C. with stirring. Then, 1.98 g of feed 2 were added batchwise and the mixture was polymerized for 15 min. Feed 1 was metered in over the course of 5 h, while the remainder of feed 2 (26.37 g) was metered in over the course of 5.5 h. When the feed was complete, the reaction mixture was heated to 70° C. and afterpolymerized for 1 h. After cooling, the polymer solution was preserved with 1.90 g of Phenonip.
Feed 1:
  122.00 g of 2-trimethylammonium ethyl methacrylate chloride (75% strength by weight), 70.00 g of CD water, 3.90 g of mercaptoethanol, 37.50 g of N-vinylpyrrolidone were adjusted to pH 8.5 with 50% strength by weight NaOH.
Feed 2:
  26.25 g of CD water, 2.10 g of Wako®V 50

Example C2

Quat311/VI/VP 82/9/9 (comparative experiment)

80.00 g of CD water, 134.84 g of feed 1 and 15.00 g of feed 2 were initially introduced, gassed with nitrogen and heated to 75° C. Upon reaching this temperature, 20.54 g of feed 3 were added and the mixture was polymerized for 15 min. The remainder of feeds 1 and 2 were then metered in over 5 hours and the remainder of feed 3 was metered in over 5.5 hours. After the end of the feed, the mixture was afterpolymerized for 1 hour and cooled, and 5.20 g of Phenonip were stirred in.

Feed 1:
  674.20 g of Quat311 (50% strength)
Feed 2:
  37.50 g of N-vinylpyrrolidone, 37.50 g of N-vinylimidazole
Feed 3:
  200.00 g of CD water, 5.40 g of Wako®V50

Example P2

TMAEMC/VI/VP 75/12.5/12.5

325.85 g of CD water, 150.00 g of 2-trimethylammonium ethyl methacrylate chloride (75% strength by weight), 18.75 g of N-vinylimidazole, 18.75 g of N-vinylpyrrolidone and 62.00 g of isopropanol were initially introduced, gassed with nitrogen and heated to 75° C. with stirring.

Then, 3.34 g of feed 1 were added in one portion and the mixture was polymerized for 15 min. The remainder of feed 1 (44.36 g) was then metered in over the course of 3.5 h.

After the end of the feed, the mixture was afterpolymerized for 1 h and then steam-distilled.

After cooling, the polymer solution was preserved with 3.15 g of Phenonip.
Feed 1:
  2.70 g of Wako®V 50 and 45.00 g of CD water Example P3

TMAEMC/VI/VP/MAA 75/9/9/7

541.50 g of CD water, 150.00 g of 2-trimethylammonium ethyl methacrylate chloride (75% strength by weight), 13.50 g of N-vinylimidazole and 10.50 g of methacrylic acid were initially introduced and adjusted to pH=8.5 with 50% strength by weight NaOH solution. Then, 13.50 g of N-vinylpyrrolidone were added and the reaction mixture, with stirring, was gassed with nitrogen and heated to 80° C. Meanwhile, 3.30 g of feed 1 were added in one portion and the mixture was polymerized for 15 min. The remainder of feed 1 (43.8 g) was metered in over the course of 2.5 h and, when the feed was complete, the mixture was afterpolymerized for a further 1 h. After cooling, the polymer solution was preserved with 3.90 g of Phenonip.
Feed 1:
  2.10 g of Wako®V50 and 45.00 g of CD water Example P3b

TMAEMC/VI/VP/MAA 75/9/9/7

541.50 g of CD water, 150.00 g of 2-trimethylammonium ethyl methacrylate chloride (75% strength by weight), 13.50 g of N-vinylimidazole and 10.50 g of methacrylic acid were initially introduced and adjusted to pH=7.0 with 50% strength by weight NaOH solution. Then, 13.50 g of N-vinylpyrrolidone were added, the pH was checked again, the reaction mixture, with stirring, was gassed with nitrogen and heated to 80° C. Then, 3.30 g of feed 1 were added batchwise and the mixture was polymerized for 15 min. The remainder of feed 1 (43.8 g) was metered in over the course of 2.5 hours and, when the feed was complete, afterpolymerized for a further 1 hour. After cooling, the polymer solution was preserved with 3.90 g of Phenonip.

Feed 1:
    2.10 g of Wako®V50 and 45.00 g of CD water

Example P3c

TMAEMC/VI/VP/MAA 75/9/9/7

541.50 g of CD water, 150.00 g of 2-trimethylammonium ethyl methacrylate chloride (75% strength by weight), 13.50 g of N-vinylimidazole and 10.50 g of methacrylic acid were initially introduced and adjusted to pH=6.0 with 50% strength by weight NaOH solution. Then, 13.50 g of N-vinylpyrrolidone were added, the pH was checked again, the reaction mixture, with stirring, was gassed with nitrogen and heated to 80° C. Then, 3.30 g of feed 1 were added batchwise and the mixture was polymerized for 15 min. The remainder of feed 1 (43.8 g) was metered in over the course of 2.5 hours and, when the feed was complete, the mixture was afterpolymerized for a further 1 hour. After cooling, the polymer solution was preserved with 3.90 g of Phenonip.
Feed 1:
    2.10 g of Wako®V50 and 45.00 g of CD water Example P4

TMAEMC/VI/VP 75/10/15

185.70 g of CD water, 115.00 g of 2-trimethylammonium ethyl methacrylate chloride (75% strength by weight), 11.50 g of N-vinylimidazole, 17.25 g of N-vinylpyrrolidone and 109.40 g of isopropanol were initially introduced, gassed with nitrogen and heated to 75° C. with stirring.

Then, 2.56 g of feed 1 were added batchwise and the mixture was polymerized for 15 min. The remainder of feed 1 (34.01 g) was then metered in over the course of 5.5 h.

When the feed was complete, the mixture was afterpolymerized for 1 h and then steam-distilled.

After cooling, the polymer solution was preserved with 2.38 g of Phenonip.
Feed 1:
    2.07 g of Wako®V 50 and 34.50 g of CD water Example P4b

TMAEMC/VI/VP 75/10/15

417.03 g of CD water, 115.00 g of 2-trimethylammonium ethyl methacrylate chloride (75% strength by weight), 11.50 g of N-vinylimidazole and 17.25 g of N-vinylpyrrolidone were initially introduced, gassed with nitrogen and heated to 80° C. with stirring.

Then, 2.56 g of feed 1 were added batchwise and the mixture was polymerized for 15 min. The remainder of feed 1 (34.01 g) was then metered in over the course of 2.5 h.

When the feed was complete, the mixture was afterpolymerized for 1 h and, after cooling, the polymer solution was preserved with 2.38 g of Phenonip.
Feed 1:
    2.07 g of Wako®V 50 and 34.50 g of CD water Example P5

TMAEMC/VI/VP 80/5/15

400.00 g of CD water and 160.00 g of 2-trimethylammonium ethyl methacrylate chloride (75% strength by weight) were added to the initial charge, gassed with nitrogen and heated to 75° C. At this temperature, 6 g of feed 1 and 2 g of feed 2 were then added batchwise and the mixture was polymerized for 15 min. The remainder of feed 1 was metered in over the course of 5 hours and the remainder of feed 2 was metered in over the course of 5.5 hours. When the feed was complete, the mixture was afterpolymerized for 1 hour and, after cooling, preserved with 1.90 g of Phenonip.
Feed 1:
    22.50 g of N-vinylpyrrolidone, 7.50 g of N-vinylimidazole
Feed 2:
    2.10 g of Wako®V 50, 26.25 g of CD water Example P6

TMAEMC/VI/VP 80/12.5/7.5

385.05 g of CD water, 160.00 g of 2-trimethylammonium ethyl methacrylate chloride (75% strength by weight), 18.75 g of N-vinylimidazole and 11.25 g of N-vinylpyrrolidone were initially introduced, gassed with nitrogen and heated to 75° C. with stirring.

Then, 3.34 g of feed 1 were added batchwise and the mixture was polymerized for 15 min. The remainder of feed 1 (44.36 g) was then metered in over the course of 5.5 h.

When the feed was complete, the mixture was afterpolymerized for 1 h. After cooling, the polymer solution was preserved with 3.15 g of Phenonip.
Feed 1:
    2.70 g of Wako®V 50 and 45.00 g of CD water Example P7

TMAEMC/VI/VP 80/10/10

385.05 g of CD water, 160.00 g of 2-trimethylammonium ethyl methacrylate chloride (75% strength by weight), 15.00 g of N-vinylimidazole and 15.00 g of N-vinylpyrrolidone were initially introduced, gassed with nitrogen and heated to 75° C. with stirring.

Then, 3.34 g of feed 1 were added batchwise and the mixture was polymerized for 15 min. The remainder of feed 1 (44.36 g) was then metered in over the course of 5.5 h.

When the feed was complete, the mixture was afterpolymerized for 1 h. After cooling, the polymer solution was preserved with 3.15 g of Phenonip.
Feed 1:
    2.70 g of Wako®V 50 and 45.00 g of CD water Example P8

TMAEMC/VI/VP 78/13.28.8

172.66 g of CD water, 156.00 g of 2-trimethylammonium ethyl methacrylate chloride (75% strength by weight), 13.20 g of N-vinylimidazole, 19.80 g of N-vinylpyrrolidone and 74.48 g of isopropanol were initially introduced, gassed with nitrogen and heated to 70° C. with stirring.

Then, 3.34 g of feed 1 were added batchwise and the mixture was polymerized for 15 min. The remainder of feed 1 (44.36 g) was then metered in over the course of 4.0 h.

When the feed was complete, the mixture was heated to 75° C. and 0.45 g of Wako®V50 in 4.00 g of CD water was added batchwise and the mixture was afterpolymerized for 1 h. Steam distillation was then carried out.

After cooling, the polymer solution was preserved with 2.45 g of Phenonip.

Feed 1:
2.70 g of Wako®V 50 and 45.00 g of CD water
Applications-Related Tests
Determination of the K Values The K values were measured in accordance with Fikentscher, *Cellulosechemie* [Cellulose Chemistry], Vol. 13, p. 58 to 64 (1932) at 25° C. in aqueous solution and are a measure of the molecular weight.

The solution of the polymers comprises 1 g of polymer in 100 ml of solution.

The K values are measured in a micro—Ubbelohde capillary type M Ic from Schott.

Wet Combability (European, Bleached Hair Tresses):
Blank value determination

Before the determination, the bleached hair tress (length about 24 cm/weight 2.7-3.3 g) was firstly shampooed twice with Texapon®NSO for a total of 1 minute and rinsed for 1 minute in order to achieve a defined wetness and swelling.

The tress was then precombed so that knots were no longer present in the hair.

The tress was then fixed to the holder and combed into the finely toothed side of the test comb using the finely toothed side of the comb. Insertion of the hair into the test comb was carried out evenly and without tension for each measurement.

The measurement was started and evaluated using the EGRANUDO® software (Frank).

The measurement was repeated 5-10 times. The measurements were carried out in a climatically controlled room at a relative humidity of about 65% and 21° C.

The calculated average was noted together with the standard deviation.

| Shampoo formulation: | |
|---|---|
| 35.70 g | Texapon ® NSO |
| 12.50 g | Tego Betain L 7 |
| 0.5 g | copolymer according to the invention, effective (0.5 g calculated as solid) |
| 0.10 g | Euxyl ® K 100 |
| ad 100 g | water |
| 1.00 g | NaCl |

5 g of the shampoo to be tested were applied, shampooed for 1 min, rinsed for 1 min, squeezed on filter paper and combed and then measurement value was determined.

Evaluation:
Decrease in combing force wet=100−(measurement value*100/blank); data in %

Instruments used: tensile/pressure testing instrument from Frank

Digital balance (top-pan balance)

Feel

During the shampooing operation of 1 minute (see above Determination of measurement value for wet combability), the foaming behavior, the foam creaminess, the care behavior and the foam volume is assessed. Afterwards, the tress is rinsed for 1 minute under running drinking water (shower spray). Using one hand, the hair tress is held open at the seam under the shower spray, with the other hand the hair is allowed to slide between thumb and palm from top to bottom. By wearing rubber gloves it is possible to sense how the hair feels as it slides along.

The waxy feel (silicone feel) of the wet hair is assessed subjectively
no waxy feel, (like untreated hair) inhibitory (+) corresponds to "poor"
slightly waxy, easy sliding (++) corresponds to "good"
waxy, very easy sliding (+++) corresponds to "very good"

The rinsed hair tress is stripped between middle finger and forefinger, squeezed on filter paper, combed and clamped into the apparatus.

Differences are detected upon combing into the combing device, i.e. the waxier the feel on the hair, the lower the resistance upon combing into the test comb. The combing force is measured analogously to the blank value determination.

Centrifuge Test:
12 g of the shampoo containing 0.5% by weight of polymer are centrifuged in a centrifuge glass for 15 minutes at about 4700 rpm and 20° C. (Multifuge 1S-R centrifuge (HERAEUS)). An apparent visual assessment is then made. Observation of a precipitate or sedimentation means that the formulation is not stable.

Storage Stability of the Shampoo:
A shampoo prepared according to the abovementioned formulation (0.5% active ingredient) was stored for 3 months at 40° C. In each case after 2 and 6 weeks and after 3 months, the shampoos were examined and investigated for possible precipitations.

| Ex. | Polymer composition | Solids content % | K value | 0.2% Al slightly waxy feel ++ 0.5% Al waxy feel +++ | Stability of shampoo (40° C.) | Wet combability hand grade | Wet combability measurement value |
|---|---|---|---|---|---|---|---|
| C1 | TMAEMC/VP 75/25 | 42.8 | 43.4 | not present | centrifuge test stable | 2+ | 44% ± 4 (0.2% Al) |
| C2 | Quat311/VI/VP 82/9/9 | 44.1 | 37.3 | not present | centrifuge test stable | 1-2 | 61% ± 3 (0.5% Al) |
| P1 | TMAEMC/VI/VP 75/12.5/12.5 | 43.8 | 57 | 0.2%: ++ | 3 months: still stable | 1− | 72% ± 1 (0.2% Al) |
| P1b | TMAEMC/VI/VP 75/12.5/12.5 | 48.5 | 50.3 | 0.5%: ++ | centrifuge test stable | 1 | 74% ± 2 (0.5% Al) |
| P2 | TMAEMC/VI/VP 75/12.5/12.5 | 24.3 | 64 | 0.5%: +++ wax feel even upon rinsing | 3 months stable, very slight precipitate | 1 | 80% ± 2; 82% ± 2 (0.5% Al) |

-continued

| Ex. | Polymer composition | Solids content % | K value | 0.2% Al slightly waxy feel ++ 0.5% Al waxy feel +++ | Stability of shampoo (40° C.) | Wet combability hand grade | Wet combability measurement value |
|---|---|---|---|---|---|---|---|
| P3 | TMAEMC/VI/VP/MAA 75/9/9/7 | 21.4 | 71.2 | 0.5%: +++wax feel only upon detangling and combing | centrifuge test stable | 1 | 76% ± 2 (0.5% Al) |
| P3b | TMAEMC/VI/VP/MAA 75/9/9/7 | 21.0 | 74.6 | 0.5%: +++ wax feel even upon rinsing | 3 mon. still stable, isolated particles, film | 1 | 80% ± 2 (0.5% Al) |
| P3c | TMAEMC/VI/VP/MAA 75/9/9/7 | 19.55 | 75.2 | 0.5%: +++ wax feel even upon rinsing | 3 mon. still stable, very slight precipitate, isolated particles | 1 | 76% ± 3 (0.5% Al) |
| P4 | TMAEMC/VI/VP 75/10/15 | 24.7 | 51.6 | 0.5%: +++ wax feel even upon rinsing | 6 weeks stable | 1 | 83% ± 2; 85% ± 2 (0.5% Al) |
| P4b | TMAEMC/VI/VP 75/10/15 | 21.0 | 81.9 | 0.5%: ++(+) wax feel even upon rinsing | 3 mon. stable, film on the glass base | 1 | 76% ± 3 (0.5% Al) |
| P5 | TMAEMC/VI/VP 80/5/15 | 26.7 | 54.5 | 0.5%: +++ wax feel even upon rinsing | 6 weeks stable | 1 | 82% ± 1 (0.5% Al) |
| P6 | TMAEMC/VI/VP 80/12.5/7.5 | 26.5 | 66.3 | 0.5%: +++ wax feel even upon rinsing | 3 mon. stable, slight precipitate | 1 | 76% ± 3 (0.5% Al) |
| P7 | TMAEMC/VI/VP 80/10/10 | 26.2 | 73.8 | 0.5%: +++ wax feel only upon detangling and combing | 3 mon. stable, slight precipitate | 1 | 76% ± 3 (0.5% Al) |
| P8 | TMAEMC/VI/V 78/13.2/8.8 | 31.9 | 63.3 | 0.5%: +++ wax feel even upon rinsing | 3 mon. stable, slight sediment | 1 | 77% ± 3 (0.5% AL) |

Shampoo Formulations/Shower Gel Formulations

Preferred shampoo formulations or shower gel formulations comprise a) 0.01 to 5% by weight of a copolymer according to the invention
b) 25 to 99.99% by weight of water
c) 0-5% by weight of a further conditioner
d) 0-30% by weight of further cosmetic constituents In addition, all anionic, neutral, amphoteric or cationic surfactants customarily used in shampoos can be used in the shampoo formulations with the above provisos.

Example 1

Conditioner Shampoo with PQ-10

| | |
|---|---|
| 35.70 g | sodium laureth sulfate |
| 6.50 g | cocamidopropylbetaine |
| 0.20 g | copolymer according to Example P1 |
| 0.40 g | polyquaternium-10 |
| 0.10 g | preservative |
| 0.10 g | perfume oil/essential oil |
| ad 100 g | aqua dem. |

Good conditioner shampoos are also obtained if, instead of the copolymer according to Example P1, one or more of the copolymers P1b, P2, P3, P3b, P3c, P4, P4b, P5, P6, P7 or P8 are used.

Example 2

Conditioner Shampoo with GHTC

| | |
|---|---|
| 35.70 g | sodium laureth sulfate |
| 6.50 g | cocamidopropylbetaine |
| 0.50 g | copolymer according to Example P1 |
| 0.20 g | guar hydroxypropyltrimonium chloride |
| 0.10 g | preservative |
| 0.10 g | perfume oil/essential oil |
| ad 100 g | aqua dem. |

Good conditioner shampoos are also obtained if, instead of the copolymer according to Example P1, one or more of the copolymers P1b, P2, P3, P3b, P3c, P4, P4b, P5, P6, P7 or P8 are used.

Example 3

Conditioner Shampoo with Polyquatemium

| | |
|---|---|
| 35.70 g | sodium laureth sulfate |
| 6.50 g | cocamidopropylbetaine |

-continued

| | |
|---|---|
| 0.20 g | copolymer according to Example P1 |
| 0.30 g | polyquaternium-44 or polyquaternium-67 |
| 0.10 g | preservative |
| 0.10 g | perfume oil/essential oil |
| ad 100 g | aqua dem. |

Good conditioner shampoos are also obtained if, instead of the copolymer according to Example P1, one or more of the copolymers P1b, P2, P3, P3b, P3c, P4, P4b, P5, P6, P7 or P8 are used.

Example 4

Shampoo

| | Phase A |
|---|---|
| 15.00 g | cocamidopropylbetaine |
| 10.00 g | disodium cocoamphodiacetate |
| 5.00 g | polysorbate 20 |
| 5.00 g | decyl glucoside |
| 0.20 g | copolymer according to Example P1 |
| 0.10 g | perfume oil/essential oil |
| q.s. | preservative |
| 2.00 g | laureth-3 |
| ad 100 | aqua dem. |
| q.s. | citric acid |
| | Phase B |
| 3.00 g | PEG-150 distearate |

Preparation

Weigh in components of phase A and dissolve; adjust pH to 6-7. Add phase B and heat to 50° C. Allow to cool to room temperature with stirring.

Good shampoos are also obtained if, instead of the copolymer according to Example P1, one or more of the copolymers P1b, P2, P3, P3b, P3c, P4, P4b, P5, P6, P7 or P8 are used.

Example 5

Shampoo

| | |
|---|---|
| 30.00 g | sodium laureth sulfate |
| 6.00 g | sodium cocoamphoacetate |
| 0.50 g | copolymer according to Example P1 |
| 3.00 g | sodium laureth sulfate, glycol distearate, cocamide MEA, laureth-10 |
| 2.00 g | dimethicone |
| q.s. | perfume |
| q.s. | preservative |
| q.s. | citric acid |
| 1.00 g | sodium chloride |
| ad 100 | aqua dem. |

Good shampoos are also obtained if, instead of the copolymer according to Example P1, one or more of the copolymers P1b, P2, P3, P3b, P3c, P4, P4b, P5, P6, P7 or P8 are used.

Example 6

Shower Gel

| | |
|---|---|
| 20.00 g | ammonium laureth sulfate |
| 15.00 g | ammonium lauryl sulfate |
| 0.50 g | copolymer according to Example P1 |
| 0.50 g | polyquaternium-7 |
| 2.50 g | sodium laureth sulfate, glycol distearate, cocamide MEA, laureth-10 |
| 0.10 g | perfume oil/essential oil |
| q.s. | preservative |
| 0.50 g | sodium chloride |
| ad 100 | aqua dem. |

Good shower gels are also obtained if, instead of the copolymer according to Example P1, one or more of the copolymers P1b, P2, P3, P3b, P3c, P4, P4b, P5, P6, P7 or P8 are used.

Example 7

Shower Gel

| | |
|---|---|
| 40.00 g | sodium laureth sulfate |
| 5.00 g | decyl glucoside |
| 5.00 g | copolymer according to Example P1 |
| 1.00 g | panthenol |
| 0.10 g | perfume oil/essential oil |
| q.s. | preservative |
| q.s. | citric acid |
| 2.00 g | sodium chloride |
| ad 100 | aqua dem. |

Good shower gels are also obtained if, instead of the copolymer according to Example P1, one or more of the copolymers P1b, P2, P3, P3b, P3c, P4, P4b, P5, P6, P7 or P8 are used.

Example 8

Shampoo

| | |
|---|---|
| 12.00 g | sodium laureth sulfate |
| 1.50 g | decyl glucoside |
| 0.50 g | copolymer according to Example P1 |
| 5.00 g | cocoglucoside glyceryl oleate |
| 2.00 g | sodium laureth sulfate, glycol distearate, cocamide MEA, laureth-10 |
| q.s. | preservative |
| q.s. | Sunset Yellow C.I. 15 985 |
| 0.10 g | perfume oil/essential oil |
| 1.00 g | sodium chloride |
| ad 100 | aqua dem. |

Good shampoos are also obtained if, instead of the copolymer according to Example P1, one or more of the copolymers P1b, P2, P3, P3b, P3c, P4, P4b, P5, P6, P7 or P8 are used.

The copolymers according to the invention are also suitable in hairstyling preparations, in particular hair foams (aerosol foams with propellant gas and pump foams without propellant gas), hairsprays (pump sprays without propellant gas) and hair gels.

Propellants are the customarily used propellants. Preference is given to mixtures of propane/butane, pentane, dimethyl ether, 1,1-difluoroethane (HFC-152 a), carbon dioxide, nitrogen or compressed air.

Aerosol Hair Foam
a) 0.1 to 10% by weight of a cosmetics polymer
b) 55 to 99.8% by weight of water and/or alcohol
c) 5 to 20% by weight of a propellant
d) 0.1 to 5% by weight of a copolymer according to the invention
e) 0 to 10% by weight of further constituents Further constituents which may be used are, inter alia, all emulsifiers customarily used in hair foams. Suitable emulsifiers may be nonionic, cationic or anionic or amphoteric.

Examples of nonionic emulsifiers (INCI nomenclature) are laureths, e.g. laureth-4; ceteths, e.g. cetheth-1, polyethylene glycol cetyl ether; cetearaths, e.g. cetheareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimmonium bromide, cocotrimonium methyl sulfate, quaternium-1 to x (INCI).

Anionic emulsifiers may, for example, be selected from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Example 9

Aerosol Hair Foam

| | |
|---|---|
| 2.00 g | cocotrimonium methosulfate |
| 0.10 g | perfume oil/essential oil |
| 3.50 g | setting polymer e.g. polyquaternium-46, PQ-44, VP/methacrylamide/vinyl imidazole copolymer, etc. |
| 0.80 g | copolymer according to Example P1 |
| q.s. | preservative |
| 75.00 g | water dem. |
| 10.00 g | propane/butane (3.5 bar) |

Good aerosol hair foams are also obtained if, instead of the copolymer according to Example P1, one or more of the copolymers P1b, P2, P3, P3b, P3c, P4, P4b, P5, P6, P7 or P8 are used.

A preparation suitable according to the invention for styling gels can, for example, have the following composition:

Styling Gel
a) 0.1 to 10% by weight of a cosmetics polymer
b) 60 to 99.85% by weight of water and/or alcohol
c) 0.05 to 10% by weight of a gel former
d) 0.1 to 5% by weight of a copolymer according to the invention
e) 0 to 20% by weight of further constituents Gel formers which can be used are all gel formers customary in cosmetics. These include lightly crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglycerides, sodium acrylates copolymer, polyquaternium-32 (and) paraffinum liquidum (INCI), sodium acrylates copolymer (and) paraffinum liquidum (and) PPG-1 trideceth-6, acrylamidopropyltrimonium chloride/acrylamide copolymer, steareth-10 alkyl ether acrylates copolymer, polyquaternium-37 (and) paraffinum liquidum (and) PPG-1 trideceth-6, polyquaternium-37 (and) propylene glycol dicaprate dicaprylate (and) PPG-1 trideceth-6, polyquaternium-7, polyquaternium-44, polyquaternium-67.

Good styling gels are also obtained if, instead of the copolymer according to Example P1, one or more of the copolymers P1b, P2, P3, P3b, P3c, P4, P4b, P5, P6, P7 or P8 are used.

Example 10

Hair Styling Gel

| | |
|---|---|
| Phase A | |
| 0.50 g | carbomer or acrylates/C10-30 alkyl acrylate crosspolymer |
| 86.40 g | water dem. |
| Phase B | |
| 0.70 g | triethanolamine |
| Phase C | |
| 6.00 g | setting polymer e.g. VP/methacrylamide/vinyl imidazole copolymer |
| 5.00 g | PVP |
| 0.20 g | PEG-25 PABA |
| 0.50 g | copolymer according to Example P1 |
| 0.10 g | perfume oil/essential oil |
| q.s. | PEG-14 dimethicone |
| q.s. | preservative |
| 0.10 g | tocopheryl acetate |

Good styling gels are also obtained if, instead of the copolymer according to Example P1, one or more of the copolymers P1b, P2, P3, P3b, P3c, P4, P4b, P5, P6, P7 or P8 are used.

Example 11

Hair Styling Gel

| | |
|---|---|
| Phase A | |
| 0.50 g | carbomer or acrylates/C10-30 alkyl acrylate crosspolymer |
| 91.20 g | water dem. |
| Phase B | |
| 0.90 g | tetrahydroxypropyl ethylenediamine |
| Phase C | |
| 7.00 g | VP/VA copolymer |
| 0.40 g | copolymer according to Example P1 |
| 0.20 g | perfume oil/essential oil |
| q.s. | preservative |
| 0.10 g | propylene glycol |

Good styling gels are also obtained if, instead of the copolymer according to Example P1, one or more of the copolymers P1b, P2, P3, P3b, P3c, P4, P4b, P5, P6, P7 or P8 are used.

Example 12

Hair Wax Cream

| | |
|---|---|
| 6.00 g | caprylic/capric triglycerides |
| 3.00 g | glyceryl stearate |
| 2.00 g | cetyl alcohol |
| 3.50 g | copolymer according to Example P1 |
| 0.50 g | cremophor A6 |
| 0.70 g | cremophor A25 |
| 0.50 g | dimethicone |
| 0.50 g | vitamin E acetate |
| 2.00 g | caprylic/capric triglyceride and sodium acrylates copolymer |
| 1.00 g | D-panthenol USP |
| 0.10 g | EDTA |
| 10.00 g | setting polymer |
| q.s. | preservative |
| ad 100 g | water dem. |

Good hair wax creams are also obtained if, instead of the copolymer according to Example P1, one or more of the copolymers P1b, P2, P3, P3b; P3c, P4, P4b, P5, P6, P7 or P8 are used.

Example 13

Hair Pudding

| | |
|---|---|
| 3.00 g | collicoat IR (BASF) |
| q.s. | preservative |
| 2.00 g | setting polymer |
| 4.00 g | acrylates/beheneth-25 methacrylate copolymer |
| 0.70 g | copolymer according to Example P1 |
| 0.50 g | dimethicone copolyol |
| 0.10 g | EDTA |
| 0.20 g | benzophenone-4 |
| ad 100 g | water dem. |

Good hair puddings are also obtained if, instead of the copolymer according to Example P1, one or more of the copolymers P1b, P2, P3, P3b, P3c, P4, P4b, P5, P6, P7 or P8 are used.

Example 14

Spray Gel

| Phase A | |
|---|---|
| 1.25 g | setting polymer |
| 96.15 g | aqua dem. |
| Phase B | |
| 0.70 g | acrylates/steareth-20 itaconate copolymer |
| 0.10 g | propylene glycol |
| 0.50 g | copolymer according to Example P1 |
| 0.10 g | glycerol |

| -continued | |
|---|---|
| 0.10 g | perfume oil/essential oil |
| q.s. | preservative |
| Phase C | |
| 0.70 g | triethanolamine |

Good spray gels are also obtained if, instead of the copolymer according to Example P1, one or more of the copolymers P1b, P2, P3, P3b, P3c, P4, P4b, P5, P6, P7 or P8 are used.

A preparation suitable according to the invention for styling sprays can, for example, have the following composition:

Example 15

Pump Hairspray

| | |
|---|---|
| 11.20 g | PEG/PPG-25/25 dimethicone/acrylates copolymer |
| 2.80 g | VP/VA copolymer |
| 1.34 g | aminomethylpropanol |
| 0.30 g | copolymer according to Example P1 |
| 0.10 g | perfume oil/essential oil |
| 11.26 g | aqua dem. |
| 73.00 g | alcohol |

Good pump hairsprays are also obtained if, instead of the copolymer according to Example P1, one or more of the copolymers P1b, P2, P3, P3b, P3c, P4, P4b, P5, P6, P7 or P8 are used.

Example 16

Pump hairspray VOC55

| | |
|---|---|
| 2.00 g | VP/methacrylamide/vinyl imidazole copolymer |
| 1.90 g | polyquaternium-46 |
| 2.00 g | copolymer according to Example P1 |
| 0.10 g | perfume oil/essential oil |
| 55.00 g | alcohol |
| 39.00 g | aqua dem. |

Good pump hairsprays VOC 55 are also obtained if, instead of the copolymer according to Example P1, one or more of the copolymers P1b, P2, P3, P3b, P3c, P4, P4b, P5, P6, P7 or P8 are used.

Skin Cosmetic Compositions

Example 17

Liquid Make-up

| Phase A | |
|---|---|
| 1.70 g | glyceryl stearate |
| 1.70 g | cetyl alcohol |
| 1.70 g | ceteareth-6 |
| 1.70 g | ceteareth-25 |
| 5.20 g | caprylic/capric triglyceride |
| 5.20 g | mineral oil or Luvitol ® Lite (INCI hydrogenated polyisobutene) |

|          | -continued |
|----------|------------|
| Phase B | |
| q.s. | preservative |
| 4.30 g | propylene glycol |
| 2.50 g | copolymer according to Example P1 |
| 59.50 g | aqua dem. |
| Phase C | |
| 0.10 g | perfume oil/essential oil |
| Phase D | |
| 2.00 g | iron oxides |
| 12.00 g | titanium dioxide |

Good liquid make-ups are also obtained if, instead of the copolymer according to Example P1, one or more of the copolymers P1b, P2, P3, P3b, P3c, P4, P4b, P5, P6, P7 or P8 are used.

Example 18

Eyeliner

|          | Phase A |
|----------|-------------|
| 40.60 g | dist. water |
| 0.20 g | disodium EDTA |
| q.s. | preservative |
| Phase B | |
| 0.60 g | xanthan gum |
| 0.40 g | veegum |
| 3.00 g | butylene glycol |
| 0.20 g | polysorbate-20 |
| Phase C | |
| 15.00 g | iron oxide/Al powder/silica (e.g. Sicopearl ® Fantastico Gold from BASF) |
| Phase D | |
| 10.00 g | aqua dem. |
| 25.00 g | setting polymer (e.g. polyurethane-1 or VP/methacrylamide/vinyl imidazole copolymer, etc.) |
| 5.00 g | copolymer according to Example P1 |

Good eyeliners are also obtained if, instead of the copolymer according to Example P1, one or more of the copolymers P1b, P2, P3, P3b, P3c, P4, P4b, P5, P6, P7 or P8 are used.

Example 19

Sunscreen Gel

|          | Phase A |
|----------|-------------|
| 0.90 g | copolymer according to Example P1 |
| 8.00 g | octyl methoxycinnamate |
| 5.00 g | octocrylene |
| 0.80 g | octyltriazone |
| 2.00 g | butylmethoxydibenzoylmethane |
| 2.00 g | tocopheryl acetate |
| 0.10 g | perfume oil/essential oil |
| Phase B | |
| 0.30 g | acrylates/C10-30 alkyl acrylate crosspolymer |
| 0.20 g | carbomer |

|          | -continued |
|----------|------------|
| 5.00 g | glycerol |
| 0.20 g | disodium EDTA |
| q.s. | preservative |
| 75.30 g | aqua dem. |
| Phase C | |
| 0.20 g | sodium hydroxide |

Good sunscreen gels are also obtained if, instead of the copolymer according to Example P1, one or more of the copolymers P1b, P2, P3, P3b, P3c, P4, P4b, P5, P6, P7 or P8 are used.

Example 20

Sunscreen Emulsion with $TiO_2$ and $ZnO_2$

|          | Phase A |
|----------|-------------|
| 1.00 g | PEG-7 hydrogenated castor oil |
| 5.00 g | copolymer according to Example P1 |
| 2.00 g | PEG-45/dodecyl glycol copolymer |
| 3.00 g | isopropyl myristate |
| 7.90 g | jojoba (*Buxus Chinensis*) oil |
| 4.00 g | octyl methoxycinnamate |
| 2.00 g | 4-methylbenzylidene camphor |
| 3.00 g | titanium dioxide, dimethicone |
| 1.00 g | dimethicone |
| 5.00 g | zinc oxide, dimethicone |
| Phase B | |
| 0.20 g | disodium EDTA |
| 5.00 g | glycerol |
| q.s. | preservative |
| 60.80 g | aqua dem. |
| Phase C | |
| 0.10 g | perfume oil/essential oil |

Good sunscreen emulsions are also obtained if, instead of the copolymer according to Example P1, one or more of the copolymers P1b, P2, P3, P3b, P3c, P4, P4b, P5, P6, P7 or P8 are used.

Example 21

Face Tonic

|          | Phase A |
|----------|-------------|
| 3.00 g | copolymer according to Example P1 |
| 0.10 g | perfume oil/essential oil |
| 0.30 g | bisabolol |
| Phase B | |
| 3.00 g | glycerol |
| 1.00 g | hydroxyethyl cetyldimonium phosphate |
| 5.00 g | witch hazel (*Hamamelis Virginiana*) distillate |
| 0.50 g | panthenol |
| q.s. | preservative |
| 87.60 g | aqua dem. |

Good face tonics are also obtained if, instead of the copolymer according to Example P1, one or more of the copolymers P1b, P2, P3, P3b, P3c, P4, P4b, P5, P6, P7 or P8 are used.

Example 22

Face Washing Paste with Peeling Effect

| Phase A | | |
|---|---|---|
| 73.00 g | aqua dem. | |
| 1.50 g | carbomer | |
| q.s. | preservative | |
| Phase B | | |
| q.s. | perfume oil | |
| 7.00 g | potassium cocoyl hydrolyzed protein | |
| 4.00 g | copolymer according to Example P1 | |
| Phase C | | |
| 1.50 g | triethanolamine | |
| Phase D | | |
| 13.00 g | polyethylene (Luwax A ™ from BASF) | |

Good face washing pastes are also obtained if, instead of the copolymer according to Example P1, one or more of the copolymers P1b, P2, P3, P3b, P3c, P4, P4b, P5, P6, P7 or P8 are used.

Example 23

Soap

| Phase A | | |
|---|---|---|
| 25.00 g | potassium cocoate | |
| 20.00 g | disodium cocoamphodiacetate | |
| 2.00 g | lauramide DEA | |
| 1.0 g | glycol stearate | |
| 2.00 g | copolymer according to Example P1 | |
| 50.00 g | aqua dem. | |
| q.s. | citric acid | |
| Phase B | | |
| q.s. | preservative | |
| 0.10 g | perfume oil/essential oil | |

Good soaps are also obtained if, instead of the copolymer according to Example P1, one or more of the copolymers P1b, P2, P3, P3b, P3c, P4, P4b, P5, P6, P7 or P8 are used.

Example 24

Face Cleansing Milk O/W Type

| Phase A | |
|---|---|
| 1.50 g | ceteareth-6 |
| 1.50 g | ceteareth-25 |
| 2.00 g | glyceryl stearate |
| 2.00 g | cetyl alcohol |
| 10.00 g | mineral oil |
| Phase B | |
| 5.00 g | propylene glycol |
| q.s. | preservative |
| 1.00 g | copolymer according to Example P1 |
| 66.30 g | aqua dem. |
| Phase C | |
| 0.20 g | carbomer |
| 10.00 g | cetearyl octanoate |
| Phase D | |
| 0.40 g | tetrahydroxypropylethylenediamine |
| Phase E | |
| 0.10 g | perfume oil/essential oil |
| 0.10 g | bisabolol |

Good face cleansing milks are also obtained if, instead of the copolymer according to Example P1, one or more of the copolymers P1b, P2, P3, P3b, P3c, P4, P4b, P5, P6, P7 or P8 are used.

Example 25

Transparent Soap

| 4.20 g | sodium hydroxide |
|---|---|
| 3.60 g | dist. water |
| 10.00 g | copolymer according to Example P1 |
| 22.60 g | propylene glycol |
| 18.70 g | glycerol |
| 5.20 g | cocoamide DEA |
| 2.40 g | cocamine oxide |
| 4.20 g | sodium lauryl sulfate |
| 7.30 g | myristic acid |
| 16.60 g | stearic acid |
| 5.20 g | tocopherol |

Good transparent soaps are also obtained if, instead of the copolymer according to Example P1, one or more of the copolymers P1b, P2, P3, P3b, P3c, P4, P4b, P5, P6, P7 or P8 are used.

Example 26

Shaving Foam

| 6.00 g | ceteareth-25 |
|---|---|
| 5.00 g | poloxamer 407 |
| 52.00 g | aqua dem. |
| 1.00 g | triethanolamine |
| 5.00 g | propylene glycol |
| 1.00 g | PEG-75 lanolin oil |
| 5.00 g | copolymer according to Example P1 |
| q.s. | preservative |
| 0.10 g | perfume oil/essential oil |
| 25.00 g | sodium laureth sulfate |

Bottling: 90 parts of active substance and 10 parts of propane/butane mixture 25:75.

Good shaving foams are also obtained if, instead of the copolymer according to Example P1, one or more of the copolymers P1b, P2, P3, P3b, P3c, P4, P4b, P5, P6, P7 or P8 are used.

Example 27

Aftershave Balm

| | Phase A |
|---|---|
| 0.25 g | acrylates/C10-30 alkyl acrylate crosspolymer |
| 1.50 g | tocopheryl acetate |
| 0.20 g | bisabolol |
| 10.00 g | caprylic/capric triglyceride |
| q.s. | perfume |
| 1.00 g | copolymer according to Example P1 |
| | Phase B |
| 1.00 g | panthenol |
| 15.00 g | alcohol |
| 5.00 g | glycerol |
| 0.05 g | hydroxyethyl cellulose |
| 1.90 g | copolymer according to Example P1 |
| 64.02 g | dist. water |
| | Phase C |
| 0.08 g | sodium hydroxide |

Good aftershave balms are also obtained if, instead of the copolymer according to Example P1, one or more of the copolymers P1b, P2, P3, P3b, P3c, P4, P4b, P5, P6, P7 or P8 are used.

Example 28

Care Cream

| | Phase A |
|---|---|
| 2.00 g | ceteareth-6 |
| 2.00 g | ceteareth-25 |
| 2.00 g | cetearyl alcohol |
| 3.00 g | glyceryl stearate SE |
| 5.00 g | mineral oil |
| 4.00 g | jojoba (*Buxus Chinensis*) oil |
| 3.00 g | cetearyl octanoate |
| 1.00 g | dimethicone |
| 3.00 g | mineral oil, lanolin alcohol |
| | Phase B |
| 5.00 g | propylene glycol |
| 0.50 g | veegum |
| 1.00 g | panthenol |
| 1.70 g | copolymer according to Example P1 |
| 6.00 g | polyquaternium-44 |
| q.s. | preservative |
| 60.80 g | aqua dem. |
| | Phase C |
| q.s. | perfume |

Good care creams are also obtained if, instead of the copolymer according to Example P1, one or more of the copolymers P1b, P2, P3, P3b, P3c, P4, P4b, P5, P6, P7 or P8 are used.

Oral and dental care preparations

Example 29

Toothpaste

| | Phase A |
|---|---|
| 34.79 g | aqua dem. |
| 3.00 g | copolymer according to Example P1 |
| 20.00 g | glycerol |
| 0.76 g | sodium monofluorophosphate |
| | Phase B |
| 1.20 g | sodium carboxymethylcellulose |
| | Phase C |
| 0.80 g | aroma oil |
| 0.06 g | saccharin |
| q.s. | preservative |
| 0.05 g | bisabolol |
| 1.00 g | panthenol |
| 0.50 g | tocopheryl acetate |
| 2.80 g | silica |
| 1.00 g | sodium lauryl sulfate |
| 7.90 g | dicalcium phosphate anhydrate |
| 25.29 g | dicalcium phosphate dihydrate |
| 0.45 g | titanium dioxide |

Good toothpastes are also obtained if, instead of the copolymer according to Example P1, one or more of the copolymers P1b, P2, P3, P3b, P3c, P4, P4b, P5, P6, P7 or P8 are used.

Example 30

Mouthwash

| | Phase A |
|---|---|
| 2.00 g | aroma oil |
| 4.50 g | copolymer according to Example P1 |
| 1.00 g | bisabolol |
| 30.00 g | alcohol |
| | Phase B |
| 0.20 g | saccharin |
| 5.00 g | glycerol |
| q.s. | preservative |
| 5.00 g | poloxamer 407 |
| 52.30 g | aqua dem. |

Good mouthwashes are also obtained if, instead of the copolymer according to Example P1, one or more of the copolymers P1b, P2, P3, P3b, P3c, P4, P4b, P5, P6, P7 or P8 are used.

Example 37

Prosthesis Adhesive

| Phase A | |
|---|---|
| 0.20 g | bisabolol |
| 1.00 g | beta-carotene |
| q.s. | aroma oil |
| 20.00 g | cetearyl octanoate |
| 5.00 g | silica |
| 33.80 g | mineral oil |
| Phase B | |
| 5.00 g | copolymer according to Example P1 |
| 35.00 g | PVP (20% strength solution in water) |

Good prosthesis adhesives are also obtained if, instead of the copolymer according to Example P1, one or more of the copolymers P1b, P2, P3, P3b, P3c, P4, P4b, P5, P6, P7 or P8 are used.

Example 38

Liquid Soap

| 15.0 g | coconut fatty acid, potassium salt |
|---|---|
| 3.0 g | potassium oleate |
| 5.0 g | Luvitol ® Lite (BASF) |
| 2.0 g | polymer of vinylpyrrolidone/stearyl methacrylate 70/30% by weight (K value 47; 1% in isopropanol) |
| 1.0 g | glycerol stearate |
| 0.5 g | copolymer according to Example P1 |
| 2.0 g | ethylene glycol distearate |
| ad 100 | specific additives, complexing agents, fragrances, water |

Good liquid soaps are also obtained if, instead of the copolymer according to Example P1, one or more of the copolymers P1b, P2, P3, P3b, P3c, P4, P4b, P5, P6, P7 or P8 are used.

Examples 39-41

Conditioning Shampoo with Pearlescence

Date in % by weight

| Additive | Ex. 39 | Ex. 40 | Ex. 41 |
|---|---|---|---|
| Copolymer according to Example P1 | 0.5 | 0.5 | 0.5 |
| Sodium laureth sulfate | 9.0 | 9.0 | 9.0 |
| Cocoamidopropylbetaine | 2.5 | 2.5 | 2.5 |
| Benzophenone-3 | 1.5 | 0.5 | 1.00 |
| Pearlizing agent | 2.0 | 2.0 | 2.0 |
| Luvitol Lite ®(BASF) | 0.1 | 0.15 | 0.05 |
| Disodium EDTA | 0.1 | 0.2 | 0.15 |

-continued

| Additive | Ex. 39 | Ex. 40 | Ex. 41 |
|---|---|---|---|
| Preservative, perfume, thickener, pH adjustment and solubility promoter | q.s. | q.s. | q.s. |
| Water | ad 100.0 | ad 100.0 | ad 100.0 |

The pH is adjusted to 6

Good conditioning shampoos with pearlescence are also obtained if, instead of the copolymer according to Example P1, one or more of the copolymers P1b, P2, P3, P3b, P3c, P4, P4b, P5, P6, P7 or P8 are used.

Examples 42-46

Formulations for Showering, Washing, Bathing

Data in % by weight

| Additive | Ex. 42 | Ex. 43 | Ex. 44 | Ex. 45 | Ex. 46 |
|---|---|---|---|---|---|
| Texapon N 70 | 13.00 | 15.00 | 10.50 | 12.50 | 10.00 |
| Dehyton PK 45 | 7.50 | 7.00 | 5.00 | 5.50 | 10.00 |
| Cetiol HE | 2.00 | 2.50 | 3.50 | 5.00 | 2.30 |
| Perfume | 0.10 | 0.10 | 0.10 | 0.10 | 0.10 |
| Luvitol ® Lite (BASF) | 1.00 | 4.50 | 7.00 | 1.40 | 3.00 |
| D-Panthenol USP | 1.00 | 1.50 | 1.80 | 1.70 | 1.40 |
| Preservative | 0.10 | 0.10 | 0.10 | 0.10 | 0.10 |
| Citric acid | 0.10 | 0.10 | 0.10 | 0.10 | 0.10 |
| Copolymer according to Example P1 | 0.50 | 1.00 | 0.50 | 0.20 | 0.10 |
| Sodium chloride | 1.50 | 1.40 | 1.40 | 1.30 | 1.50 |
| Water dem. | ad 100 | ad 100 | ad 100 | ad 100 | ad 100 |

Good formulations for showering, washing, bathing are also obtained if, instead of the copolymer according to Example P1, one or more of the copolymers P1b, P2, P3, P3b, P3c, P4, P4b, P5, P6, P7 or P8 are used.

The invention claimed is:
1. A copolymer obtainable by polymerization of
  a) at least 60% by weight of one α,β-ethylenically unsaturated monomer a) of the general formula V

$$R^{14}\text{---}\underset{\underset{O}{\|}}{\overset{R^{15}}{C}}\text{---}Z\text{---}R^{18}\text{---}\overset{R^{27}}{\underset{[R^{17}]_g}{\overset{|}{N}}}R^{25}R^{26} \quad An \qquad (V)$$

where
  $R^{14}$ and $R^{15}$, independently of one another, are selected from the group consisting of hydrogen, $C_1$-$C_8$ linear- or branched-chain alkyl, methoxy, ethoxy, 2-hydroxyethoxy, 2-methoxyethoxy and 2-ethoxyethyl,
  $R^{17}$ is hydrogen or methyl,
  $R^{18}$ is alkylene or hydroxyalkylene having 1 to 24 carbon atoms, optionally substituted by alkyl,
  g is 0 or 1,
  Z is nitrogen when g=1 or oxygen when g=0,
  $R^{25}$ and $R^{26}$ are in each case and independently of one another selected from the group consisting of hydrogen, $C_1$-$C_{40}$ linear- or branched-chain alkyl, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl, $R^{27}$ is H or $C_1$-$C_4$ alkyl, An is a halogen ion, $CH_3SO_4^-$, $C_2H_5SO_4^-$, or $(SO_4^{2-})_{0.5}$, b) at least one α,β-ethylenically unsaturated monomer b) of the general formula II

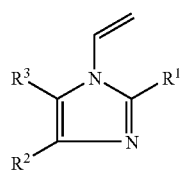

where $R^1$ to $R^3$, independently of one another, are hydrogen, $C_1$-$C_4$-alkyl or phenyl;

c) at least one α,β-ethylenically unsaturated monomer c) of the general formula III

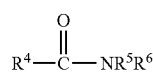

where one of the radicals $R^4$ to $R^6$ is a group of the formula $CH_2=CR^7$— where $R^7$=H or $C_1$-$C_4$-alkyl and the other radicals $R^4$ to $R^6$, independently of one another, are H, alkyl, cycloalkyl, heterocycloalkyl, aryl or hetaryl, where $R^4$ and $R^5$, together with the amide group to which they are bonded may also be a lactam having 5 to 8 ring atoms, and where $R^5$ and $R^6$, together with the nitrogen atom to which they are bonded, may also be a five- to seven-membered heterocycle.

2. The copolymer according to claim 1, where at least one monomer a) is selected from the group consisting of quaternized N,N-dimethylaminoalkyl(meth)acrylamides, quaternized N,N-dimethylaminoalkyl (meth)acrylic esters and mixtures thereof.

3. The copolymer according to claim 1, where at least one monomer a) is selected from the group consisting of quaternized N-[3-(dimethylamino)propyl]meth-acrylamide, quaternized N,N-dimethylaminoethyl methacrylate and mixtures thereof.

4. The copolymer according to claim 1, where at least one monomer b) is N-vinylimidazole.

5. The copolymer according to claim 1, where at least one monomer c) is selected from the group consisting of N-vinylpyrrolidone, N-vinylcaprolactam and mixtures thereof.

6. The copolymer according to claim 1, obtainable by polymerization of
a) 60-90% by weight of monomer a)
b) 5-35% by weight of monomer b)
c) 5-35% by weight of monomer c)
d) 0 to 20% by weight of monomer d),
in each case based on the total weight of the monomers used for the polymerization,
with the proviso that the sum of the amounts of the monomers a) to d) is 100% by weight.

7. The copolymer according to claim 1, obtainable by polymerization of
a) 70-80% by weight of monomer a)
b) 10-20% by weight of monomer b)
c) 10-20% by weight of monomer c)
d) 0 to 10% by weight of monomer d)
in each case based on the total amount of the monomers a) to d), with the proviso that the sum of the amounts of the monomers a) to d) is 100% by weight.

8. The copolymer according to claim 1, where monomer d) is or comprises an anionic or anionogenic compound.

9. The copolymer according to claim 1, where component d) is or comprises methacrylic acid.

10. A cosmetic or pharmaceutical composition comprising
A) at least one copolymer as defined in claim 1 and
B) at least one cosmetically acceptable carrier.

11. The composition according to claim 10, where component B) is selected from
i) water,
ii) water-miscible organic solvents,
iii) oils, fats, waxes,
iv) esters of $C_6$-$C_{30}$-monocarboxylic acids with mono-, di- or trihydric alcohols that are different from iii),
v) saturated acyclic and cyclic hydrocarbons,
iv) fatty acids,
vii) fatty alcohols,
viii) propellant gases
and mixtures thereof.

12. The composition according to claim 10, comprising at least one additive different from components A) and B) which is selected from cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, consistency regulators, humectants, refatting agents, collagen, protein hydrolyzates, lipids, antioxidants, antifoams, antistats, emollients and softeners.

13. The composition according to claim 10 in the form of a spray, gel, foam, mousse, ointment, cream, emulsion, suspension, lotion, milk or paste.

14. A hair rinse or hair shampoo comprising a copolymer as defined in claim 1.

15. A composition as claimed in claim 10, wherein the composition is present in a skin cleansing composition, a composition for the care and protection of the skin, a nail care composition, a preparation for a decorative cosmetic, and in a hair treatment composition.

16. The composition according to claim 15, wherein the composition is present in a hair treatment composition as a setting agent and/or as a conditioner.

17. The composition according to claim 16, where the composition is in the form of a hair gel, shampoo, setting foam, hair tonic, hairspray or hair foam.

18. A composition comprising the copolymer according to claim 1, wherein the composition is an auxiliary is present in (a) coating composition for solid drug forms, modifies rheological properties, is a surface-active compound is present in an adhesive, or is present in a coating composition used in textile industry, paper industry, printing industry, or leather industry.

19. The copolymer according to claim 1 further comprising at least one further free-radically polymerizable monomer d) different from a), b) and c).

20. The copolymer according to claim 1, wherein $R^{18}$ is optionally substituted by $C_2H_4$, $C_3H_6$, $C_4H_8$, or $CH_2$—CH(OH)—$CH_2$.

21. The copolymer according to claim 1, wherein $R^{27}$ is $C_1$-$C_4$ alkyl.

22. The copolymer according to claim 21, wherein $R^{27}$ is methyl or ethyl.

23. The copolymer according to claim 1, wherein An is a chloride.

\* \* \* \* \*